(12) United States Patent
Webb et al.

(10) Patent No.: US 10,954,208 B2
(45) Date of Patent: Mar. 23, 2021

(54) METHOD FOR SYNTHESIS OF CANNABIS PRODUCTS

(71) Applicant: Plantbiosis Ltd., Lethbridge (CA)

(72) Inventors: Dylan James Webb, Lethbridge (CA); Paul George Hayes, Lethbridge (CA); Igor Kovalchuk, Lethbridge (CA)

(73) Assignee: PLANTBIOSIS LTD., Lethbridge (CA)

( * ) Notice: Subject to any disclaimer, the term of this patent is extended or adjusted under 35 U.S.C. 154(b) by 0 days.

(21) Appl. No.: 16/789,467

(22) Filed: Feb. 13, 2020

(65) Prior Publication Data
US 2020/0262806 A1 Aug. 20, 2020

Related U.S. Application Data

(60) Provisional application No. 62/806,464, filed on Feb. 15, 2019, provisional application No. 62/913,041, filed on Oct. 9, 2019.

(51) Int. Cl.
*A61K 36/00* (2006.01)
*C07D 311/78* (2006.01)
*C07C 37/00* (2006.01)

(52) U.S. Cl.
CPC .......... *C07D 311/78* (2013.01); *C07C 37/004* (2013.01)

(58) Field of Classification Search
CPC ..................................................... A61K 36/00
USPC ........................................................ 424/725
See application file for complete search history.

(56) References Cited

PUBLICATIONS

Pollastro et al., Journal of Natural Products, 2018, 81, pp. 630-633.*
Lopatriello et al., Bioorganic and Medicinal Chemistry, 26, 2018, 4532-4536.*

* cited by examiner

*Primary Examiner* — Michael V Meller
(74) *Attorney, Agent, or Firm* — Eva Taksel

(57) ABSTRACT

The present invention provides methods of extraction of at least one cannabinoid from an initial *cannabis* biomass in "one-pot" step using toluene to form a toluene extract and using the toluene extract for producing high concentrations of Δ-9-tetrahydrocannabinol (Δ9THC) and/or cannabinol (CBN) of a purity of at least 75% and at a yield of at least 75% by weight of the at least one cannabinoid from the initial *cannabis* biomass in the toluene extract.

11 Claims, 18 Drawing Sheets

METHOD FOR SYNTHESIS OF CANNABIS PRODUCTS

FIELD OF THE INVENTION

The present invention relates generally to chemical synthesis of phytocannabinoids.

BACKGROUND OF THE INVENTION

Phytocannabinoids are lipophilic compounds biosynthesized in *Cannabis sativa*. There are many different phytocannabinoids, including Δ-9-tetrahydrocannabinol ("Δ9THC") and cannabidiol ("CBD"), which are initially synthesized in *C. sativa* as Δ-9-tetrahydrocannabinolic acid ("Δ9THCa") and cannabidiolic acid ("CBDa"). Phytocannabinoids have a variety of applications, including potential anti-cancer, pain-killing, anti-inflammatory, anti-spastic and other properties. Hemp varieties of *C. sativa* that can be cultivated generally include less than 0.3% Δ9THC in dry flowers and about 1.0-2.0% CBD. Drug-type varieties of *C. sativa* have higher concentrations of Δ9THCa and some varieties have higher concentrations of CBDa.

Hemp varieties of *C. sativa* with higher CBDa biosynthesis are expected to come to market and will improve availability of CBDa and CBD, but not Δ9THCa and Δ9THC. Regulatory restrictions in most jurisdictions that allow commercial cultivation and commercial sale of drug-type varieties of *C. sativa* for medical purposes generally prevent large scale outdoor cultivation of drug-type cultivars, which will keep the Δ9THCa percentages low in hemp varieties of *C. sativa*.

Many different medicinal properties are due to the effect of Δ9THC and Δ9THCa. Application of Δ9THC is complicated by the psycho-activity associated with this phytocannabinoid. The psycho-activity complicates achievement of a therapeutic dose because of an emphasis on avoiding psychoactive effects.

Cannabinol ("CBN") is a known degradation product of Δ9THC and is considered to be a phytocannabinoid. CBN has very low psychoactive property, but retains other biological properties. In particular, there is interest in application of CBN to products that are intended to assist users in falling asleep. CBN may also substitute Δ9THC for cancer therapy; numerous reports demonstrated anti-cancer properties of both compounds. CBN can be obtained by long-term exposure of Δ9THC to air. Degradation Δ9THC to CBN is generally slow and inefficient but can be enhanced by heating.

In one previous study, degradation of Δ9THC when heated for approximately 75 to 90 min was 2.8% w/w at 120° C., 5.1% w/w at 160° C., and 5.7% w/w at 200° C., respectively. Not all product of degradation of Δ9THC is CBN. At 120° C., only 9.0% w/w of the Δ9THC that was degraded resulted in CBN. At 160° C., only 7.8% w/w of the Δ9THC that was degraded resulted in CBN. However, when the temperature increased to 200° C., 29.1% w/w of all Δ9THC that was degraded resulted in CBN (Repka et al., 2006).

In a more recent study, conversion of various cannabinoids, including CBD and cannabidivarin ("CBDV"), demonstrated that one of the products of conversion was CBN. The conversion rate of pure CBD was reported at 72%. Direct conversion from CBDV-rich extract resulted in a very small fraction of CBN. Specifically, 25 mg of CBN and 150 mg of cannabivarin ("CBNV" or "CBV") was obtained from 2 g of CBDV rich extract (the concentration of CBDV was not mentioned) (Pollastro et al., 2018).

In the method applied by Pollastro et al., 2018, the major contributing to this reaction include CBD, CBDa, Δ9THC and THCa. Aromatization of the saturated ring in these compounds is catalyzed by the presence of $I_2$. This process produces the HI, which catalyzes the ring closure of CBD and CBDa to produce Δ9THC and THCa respectively. Elevated temperatures cause decarboxylation of both CBDa and THCa, to CBD and Δ9THC, respectively. Formation of Δ9THC from CBD and from THCa follows, and formation of CBN from Δ9THC. This previous art method includes multiple steps of adding solvent and iodine (FIG. 1).

In one previous study, cannabinoids are purified with the use of ethanol through multi-step reactions including heating, wash in polar solvent, extracting in ethanol or ethyl acetate, purifying it with chromatography and measuring the extract concentration with mass spectrometry (Marshall, Campbell WO 2019/100172 A1).

There thus remains an unmet need to provide fully compatible improved methods for extracting, synthesizing and isolating phytocannabinoid compounds and compounds derived from phytocannabinoids.

SUMMARY OF THE INVENTION

The present invention provides a method for extraction of phytocannabinoids from *Cannabis sativa* biomass using toluene in a "one-pot" reaction, producing an enriched cannabinoids extract.

The present invention further provides methods of extraction of at least one cannabinoid from an initial *cannabis* biomass in "one-pot" step using toluene to form a toluene extract and using the toluene extract for producing high concentrations of Δ-9-tetrahydrocannabinol (Δ9THC) and/or cannabinol (CBN) of a purity of at least 75% and at a yield of at least 75% by weight of the at least one cannabinoid in the toluene extract.

The methods of the present invention combine extraction protocols of at least one cannabinoid, together with a catalytic conversion of an extracted cannabinoid mixture to Δ9THC and/or CBN in a "one-pot" process.

The present invention further provides methods for combining the extraction protocols with the catalytic conversion of extracted cannabinoid mixtures into Δ9THC and/or CBN into a "one-pot" reaction.

There is thus provided according to an embodiment of the present invention, a method of extracting cannabinoids in "one-pot" step, the method including:

a. mixing toluene and *cannabis* biomass to form a toluene-biomass mixture;

b. filtering the toluene-biomass mixture to elute a toluene solution;

c. optionally repeating the previous step twice;

d. optionally combining the eluted toluene solutions; and e. removing all volatiles in vacuo to yield a thick brown oil enriched in CBDa and THCa.

The present invention provides methods of extraction of cannabinoids from initial *cannabis* biomass in "one-pot" step using toluene and using the extract for producing high concentrations of Δ-9-tetrahydrocannabinol (Δ9THC) and/or cannabinol (CBN). Non-polar solvent was added to the cannabinoid extract and stirred at a temperature of −10° C. in presence of boron trifluoride etherate to form a product mixture and extracting the product mixture to produce Δ9THC of a purity of at least 85% at the yield of at least 75%.

In a "one-step" reaction, non-polar solvent was added to the cannabinoids extract at a temperature of 130° C. in presence of a defined ratio of $I_2$ relative to the at least one phytocannabinoid for a predetermined time to form a product mixture and extracting the product mixture to produce CBN of a purity of at least 75% at a yield of at least 75% by weight of the at least one phytocannabinoid in the reagent mixture.

According to one embodiment, crude extraction includes the following steps:

a) the step of weighing biomass and crushing it with mortar and pestle;

b) the step of adding toluene to *cannabis* biomass in the Erlenmeyer flask and stirring it vigorously for 20 minutes;

c) the step of filtering the toluene/biomass mixture through Buchner funnel;

d) repeating the previous step two times;

e) combining toluene solutions from three washing steps and removing all volatiles in vacuo to yield a thick brown oil enriched in CBDa and THCa.

In one specific case, using quantitative NMR, the extract was found to be 45.2% CBD-A and 1.2% THC-A.

In further embodiment, the present invention provides a method producing cannabinol (CBN), the method including reacting, in a "one-step" reaction, a reagent mixture, including at least one phytocannabinoid in a non-polar solvent at a temperature of 130° C. in a defined ratio of $I_2$ relative to the at least one phytocannabinoid for a predetermined time to form a product mixture and extracting the product mixture to produce CBN of a purity of at least 75% at a yield of at least 75% by weight of the at least one phytocannabinoid in the reagent mixture.

There is thus provided according to an embodiment of the present invention, a method of producing cannabinol (CBN) including;

a) dissolving extract reach in cannabinoids in toluene, using 20 mL toluene for 564.5 mg of extract;

b) adding 282.3 mg iodine (50% of the volume of extract) into the "one-step" reaction and fitting the round-bottom flask with a reflux condenser;

c) submerging the flask into oil bath, and stirring the reaction for three hours under the temperature of 130° C.;

d) cooling the flask to room temperature and washing with a saturated solution of sodium thiosulfate (3×30 mL);

e) washing the combined aqueous layer with toluene (20 mL), combining organic layers and drying with magnesium sulfate;

f) removing volatile compounds in vacuo to produce a crude brown oil;

g) purifying oil with column chromatography using silica gel as the stationary phase (30 mL) and a 9:1 solution of petroleum ether:diethyl ether as the eluent.

h) extracting the product mixture to produce CBN (that moves through the column as the fourth fraction) of a purity of at least 75% at a yield of at least 20% from the reagent mixture.

Additionally, according to an embodiment of the present invention, the reagent mixture includes an extract from *Cannabis sativa*.

Furthermore, according to an embodiment of the present invention, the reaction is "one-step" procedure.

Moreover, according to an embodiment of the present invention, the reagent mixture includes at least one phytocannabinoid.

Additionally, according to an embodiment of the present invention, wherein the at least one phytocannabinoid includes at least 40% (w/w) Δ-9-tetrahydrocannabinol Δ9THC.

Additionally or alternately, according to an embodiment of the present invention, the at least one phytocannabinoid includes at least 40% (w/w) Δ-9-tetrahydrocannabinolic acid (Δ9THCa).

Additionally or alternately, according to an embodiment of the present invention, the at least one phytocannabinoid include at least 40% (w/w) cannabidiol (CBD).

Furthermore, according to an embodiment of the present invention, the at least one phytocannabinoid includes at least 40% (w/w) cannabidiolic acid (CBDa).

Further, according to an embodiment of the present invention, the reagent mixture includes iodine ($I_2$).

Moreover, according to an embodiment of the present invention, the non-polar solvent includes a non-polar solvent with a normal boiling point above 100° C.

Further, according to an embodiment of the present invention, the non-polar solvent includes toluene.

Furthermore, according to an embodiment of the present invention, the reaction is set in the flask under high pressure, allowing to reach the temperature of 130° C.

Importantly, according to an embodiment of the present invention, the purity of the CBN produced by the method of the present invention, is at least 78%, at least 80%, at least 85%, at least 90%, at least 91%, at least 92%, at least 93%, at least 94%, at least 95%, at least 96%, at least 97%, at least 98% or at least 99%.

Additionally, according to an embodiment of the present invention, the yield of CBN is at least 12%, at least 14%, at least 16%, at least 18%, or at least 20% of a total initial biomass weight including the at least one phytocannabinoid.

Importantly, according to an embodiment of the present invention, the yield of CBN is at least 60%, at least 70%, at least 80%, at least 85%, or at least 90% by weight of the at least one phytocannabinoid in the reagent mixture.

Furthermore, according to an embodiment of the present invention, the amount of $I_2$ relative to the phytocannabinoids in the reagent mixture includes a w/w ratio of at least 30% of the weight of the at least one phytocannabinoid in the reagent mixture.

Moreover, according to an embodiment of the present invention, the amount of $I_2$ relative to the at least one phytocannabinoid in the reagent mixture includes a w/w ratio of at least 40% of the weight of the at least one phytocannabinoid in the reagent mixture.

In some cases, according to an embodiment of the present invention, the amount of $I_2$ relative to the at least one phytocannabinoid in the reagent mixture includes a w/w ratio of at least 50% of the weight of the at least one phytocannabinoid in the reagent mixture.

Furthermore, according to an embodiment of the present invention, the reacting step includes stirring the reaction mixture for a reaction time of between 1 and 2 hours.

Furthermore, according to an embodiment of the present invention, wherein stirring the reaction mixture includes stirring the reaction mixture for at least three hours.

Yet further, according to an embodiment of the present invention, the reacting step includes stirring the reaction mixture for a reaction time of between 1 and 4 hours.

Additionally, according to an embodiment of the present invention, the extracting step includes washing the product mixture with an aqueous wash solution to form a washed product phase.

Furthermore, according to an embodiment of the present invention, the aqueous wash solution includes at least one of saturated aqueous sodium hydrogen carbonate and aqueous sodium thiosulfate.

Moreover, according to an embodiment of the present invention, the extracting step further includes drying the washed product phase with at least one drying agent.

Additionally, according to an embodiment of the present invention, the at least one drying agent includes magnesium sulfate.

Moreover, according to an embodiment of the present invention, magnesium sulfate that is used is extra dry and is kept under inert argon or nitrogen atmosphere.

Furthermore, according to an embodiment of the present invention, the extracting step further includes eluting the CBN under vacuum.

In some cases, according to an embodiment of the present invention, the method further includes purifying the CBN with column chromatography, using silica gel as the stationary phase and a 9:1 solution of petroleum ether:diethyl ether as the eluent.

In further embodiment, the present invention provides a method producing Δ-9-tetrahydrocannabinol (Δ9THC) from cannabidiol (CBD).

Additionally, according to an embodiment of the present invention, the method includes a) reacting a reagent mixture step includes reacting CBD and a catalyst, in a non-polar solvent in a well-sealed flask under vacuum under an inert gas atmosphere selected from argon (preferably) or nitrogen at a temperature of between −20° C. and 0° C. for a period of time, to form a Δ-9-tetrahydrocannabinol mixture; and b) extracting the Δ-9-tetrahydrocannabinol mixture to yield at least 70% Δ-9-tetrahydrocannabinol from the cannabidiol (CBD).

Furthermore, according to an embodiment of the present invention, the extracting step further includes;

i. adding aqueous sodium hydrogen carbonate to the Δ-9-tetrahydrocannabinol mixture, resulting in separation of the reaction mixture into an aqueous phase and a non-polar phase;

ii. washing the non-polar phase;

iii. drying the non-polar phase with a drying agent; and iv. eluting Δ9THC from the non-polar phase under vacuum and purifying the Δ9THC.

Further, according to an embodiment of the present invention, the reagent mixture includes an extract from *Cannabis sativa*.

Additionally, according to an embodiment of the present invention, the non-polar solvent includes dichloromethane.

Furthermore, according to an embodiment of the present invention, the non-polar solvent includes chloroform.

Further, according an embodiment of the present invention, the temperature of the extraction is between 15° C. and 25° C. in at least part of the extracting step.

Moreover, according to an embodiment of the present invention, the extraction temperature is 20° C.

Furthermore, according to an embodiment of the present invention, the catalyst includes boron trifluoride etherate.

Further, according to an embodiment of the present invention, the temperature of catalysis reaction is between −15° C. and −5° C. in at least part of the extracting step.

Moreover, according to an embodiment of the present invention, the temperature is −10° C.

Further, according to an embodiment of the present invention, the period of time of catalyst reaction is at least three hours.

Yet further, according to an embodiment of the present invention, the aqueous sodium hydrogen carbonate includes saturated aqueous sodium hydrogen carbonate.

Furthermore, according to an embodiment of the present invention, washing the non-polar phase includes washing the non-polar phase with deionized water.

Further, according to an embodiment of the present invention, the drying agent includes magnesium sulfate.

Additionally, according to an embodiment of the present invention, purifying the Δ9THC includes purifying the Δ9THC with column chromatography, using silica gel as the stationary phase and a 1:1 solution of petroleum ether: diethyl ether as the eluent.

The present invention will be more fully understood from the following detailed description of the preferred embodiments thereof, taken together with the drawings and appendices.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Embodiments of the present disclosure will now be described, by way of example only, with reference to the attached Figures.

Figure 1:
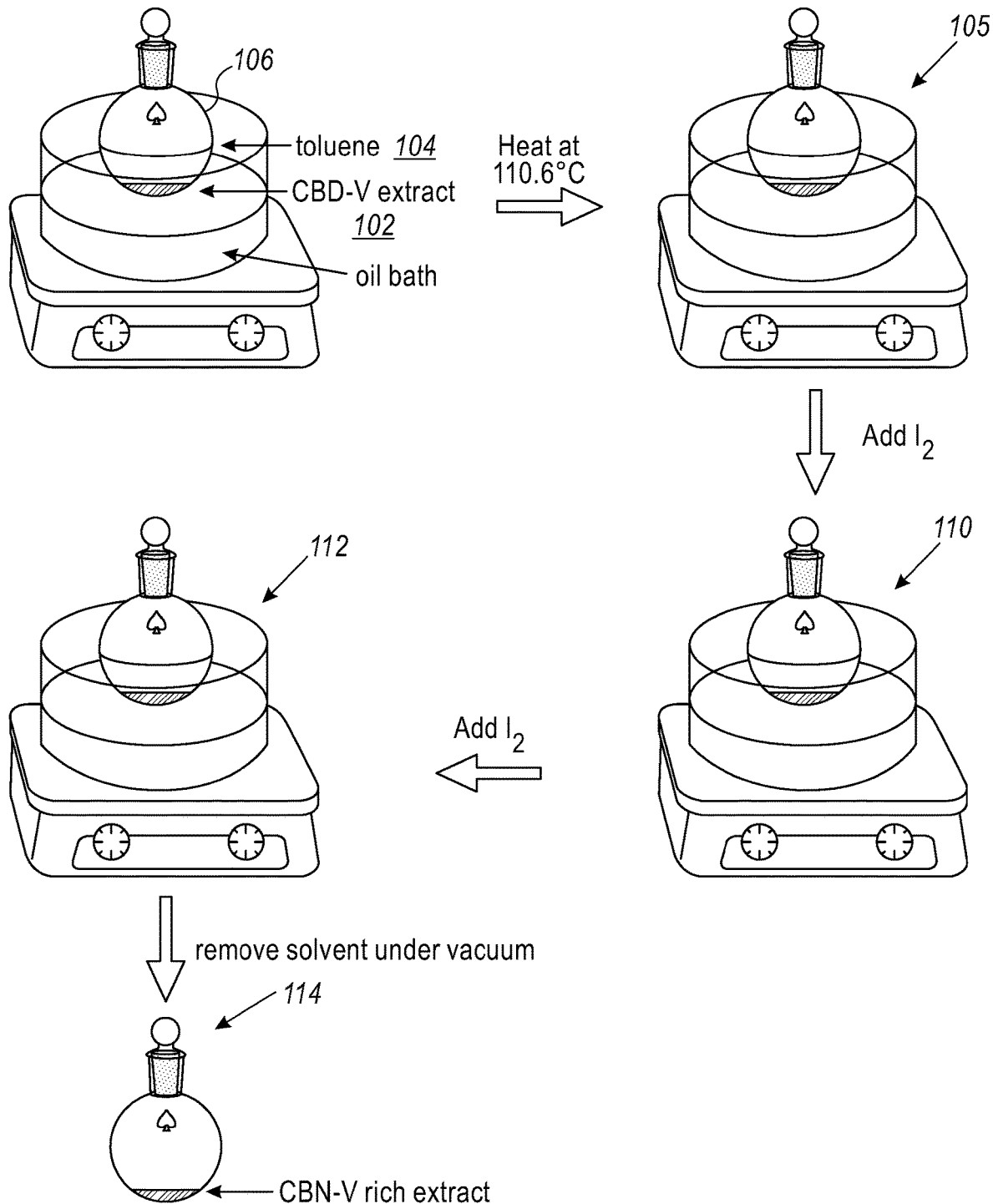

FIG. 1 is a simplified pictorial illustration of a prior art method of synthesizing CBV (CBN-V).

Figure 2A:
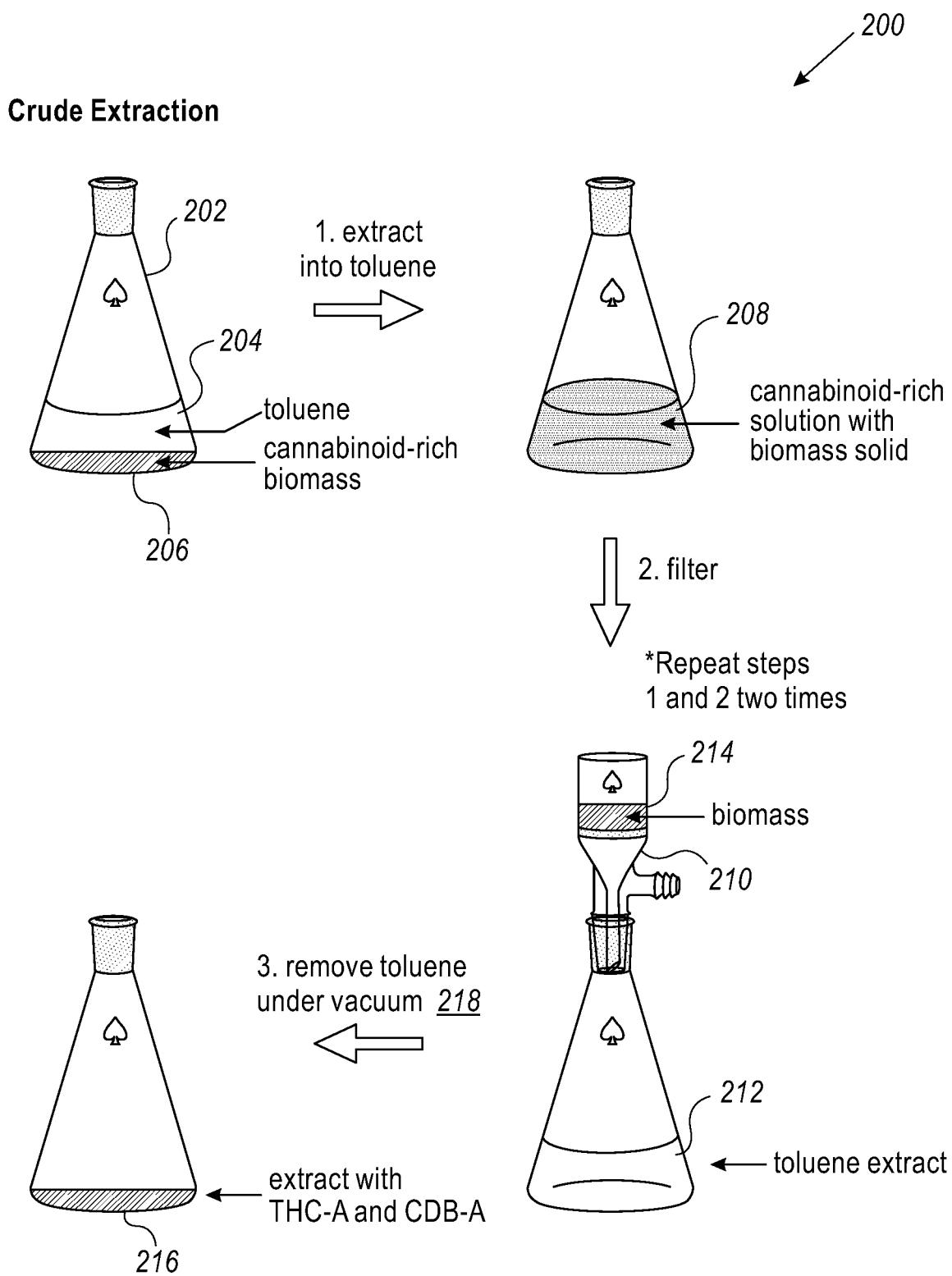
Figure 2B:
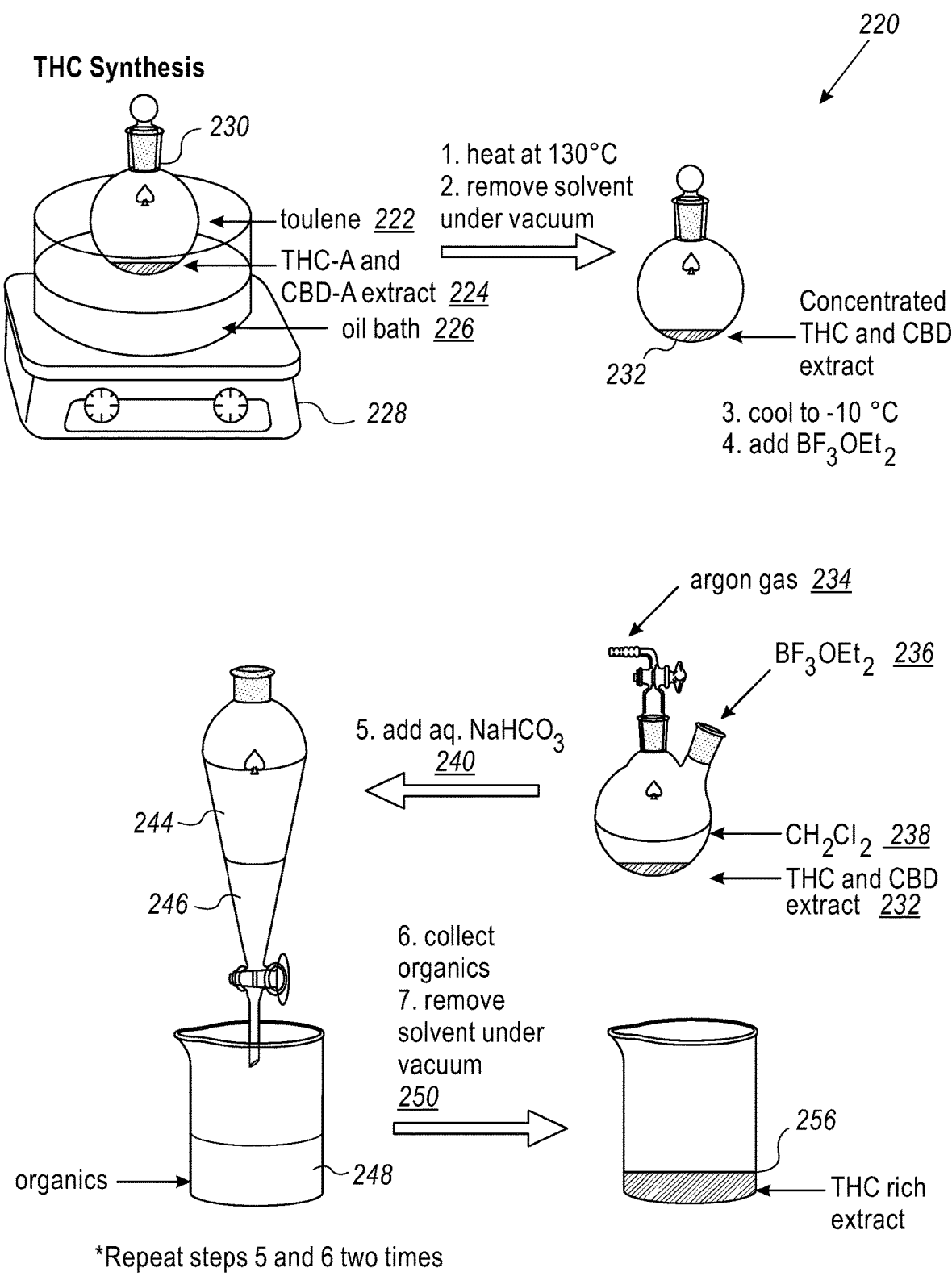
Figure 2C:
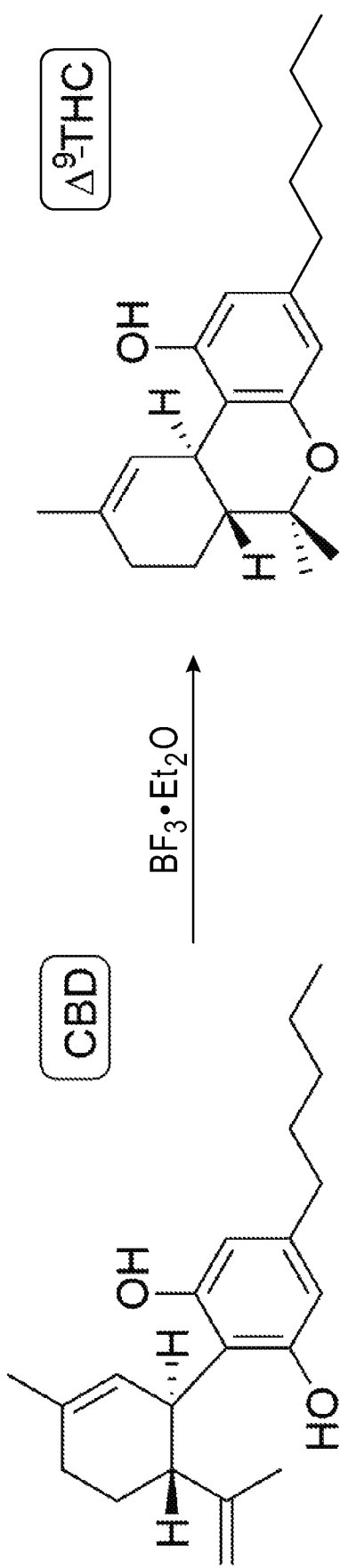
Figure 2C:
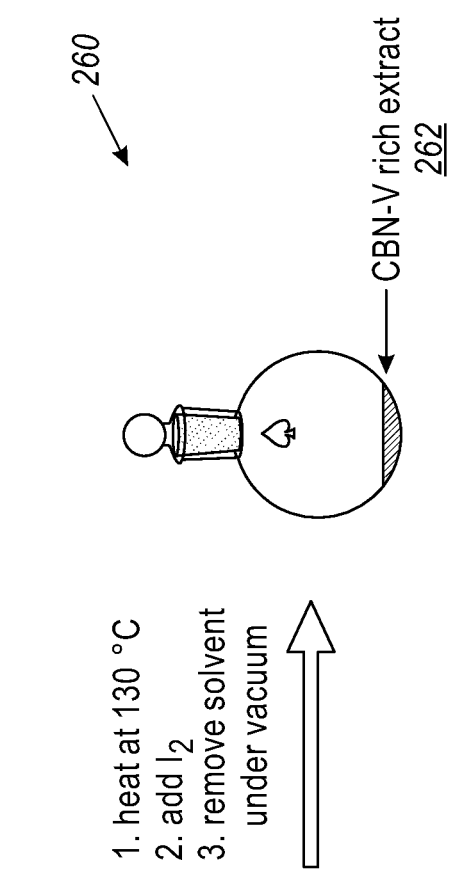
Figure 2D:
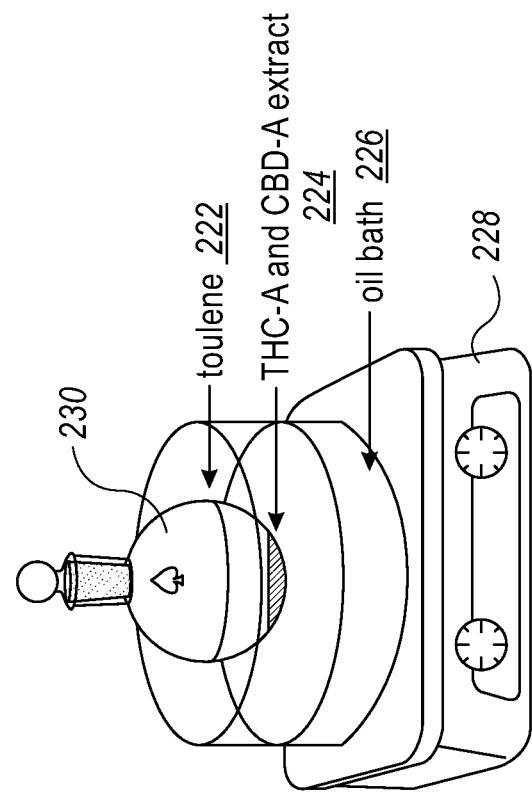
Figure 2E:
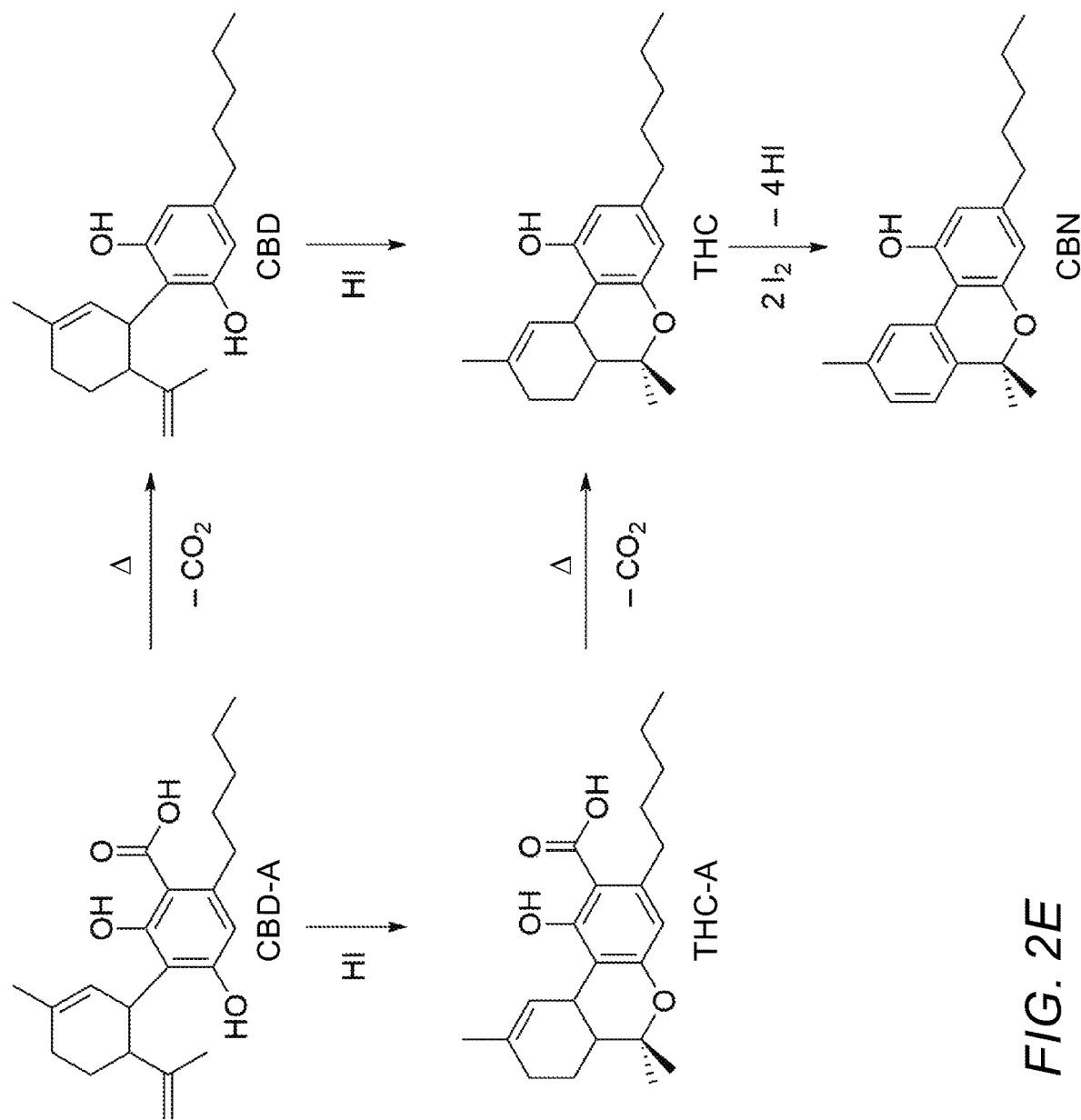
Figure 2F:
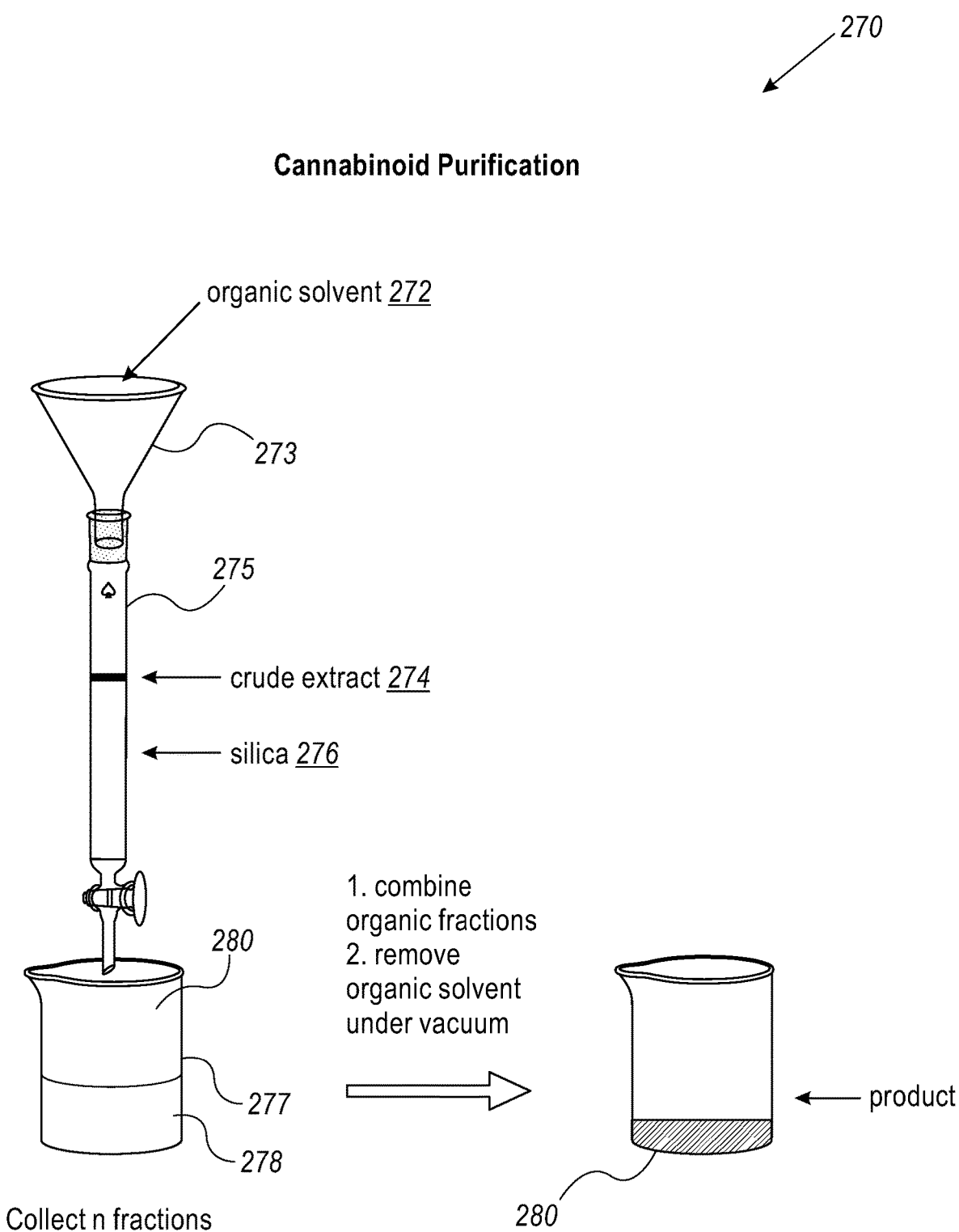
Figure 3:
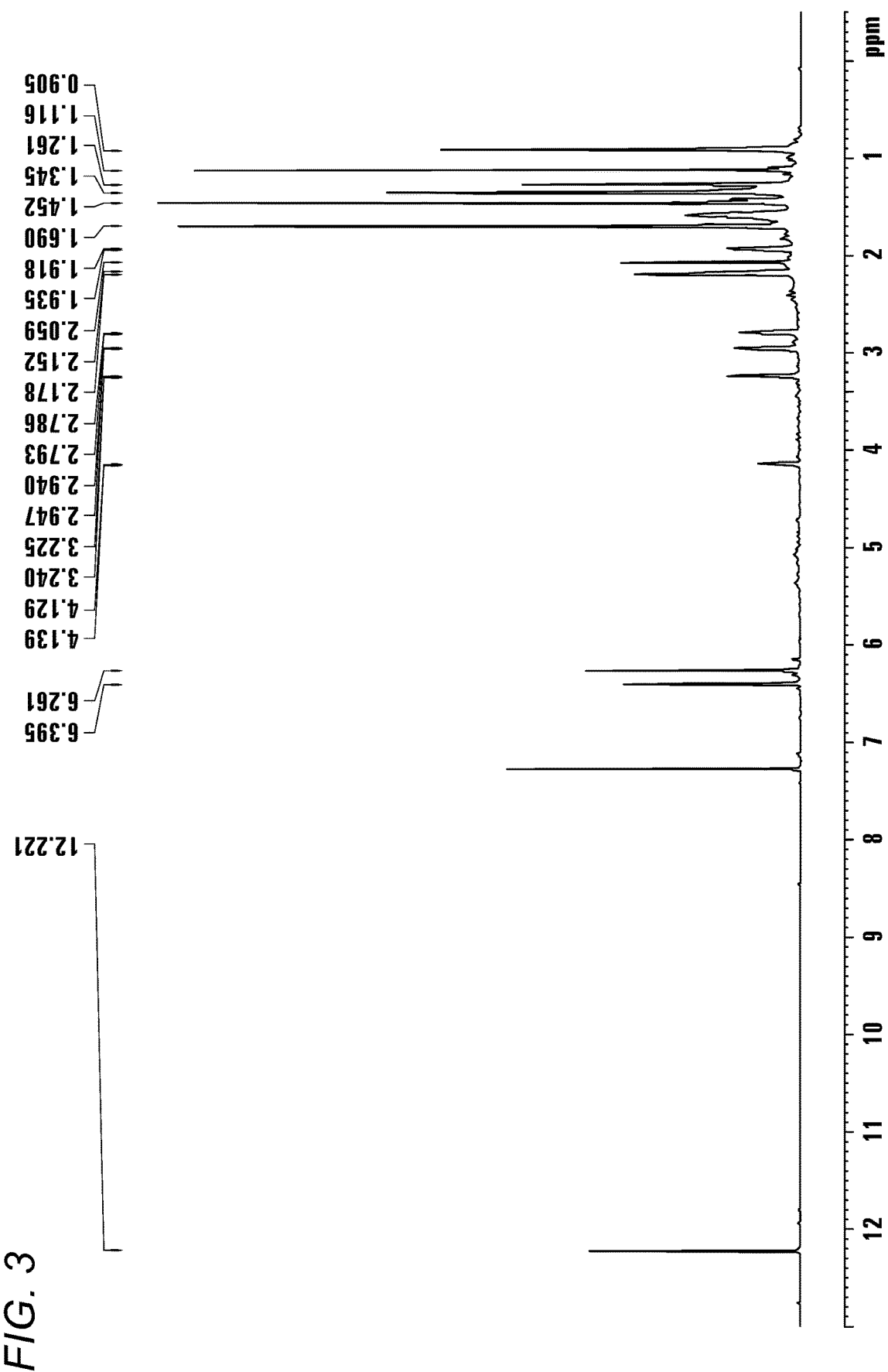
Figure 4:
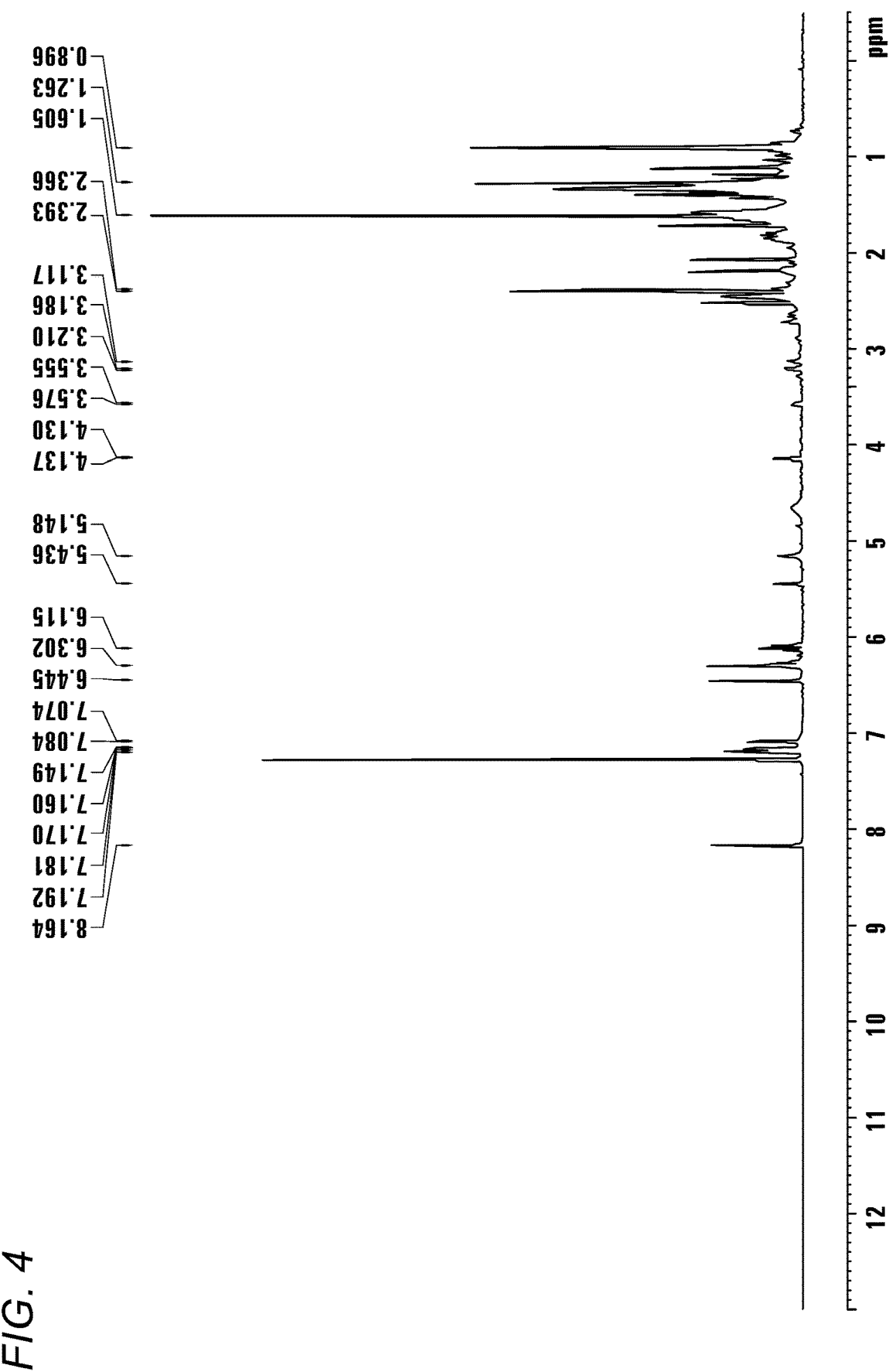
Figure 5:
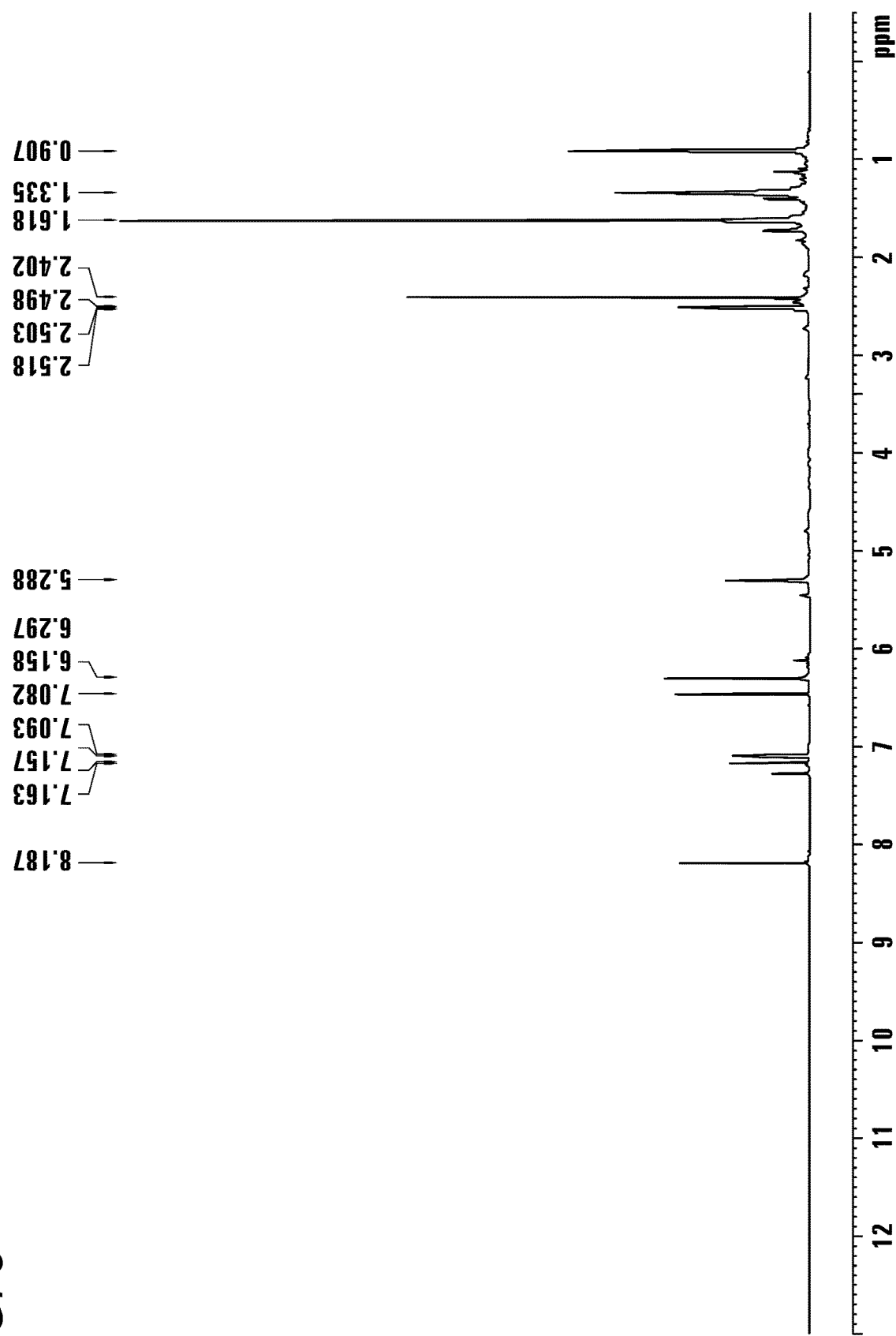
Figure 6:
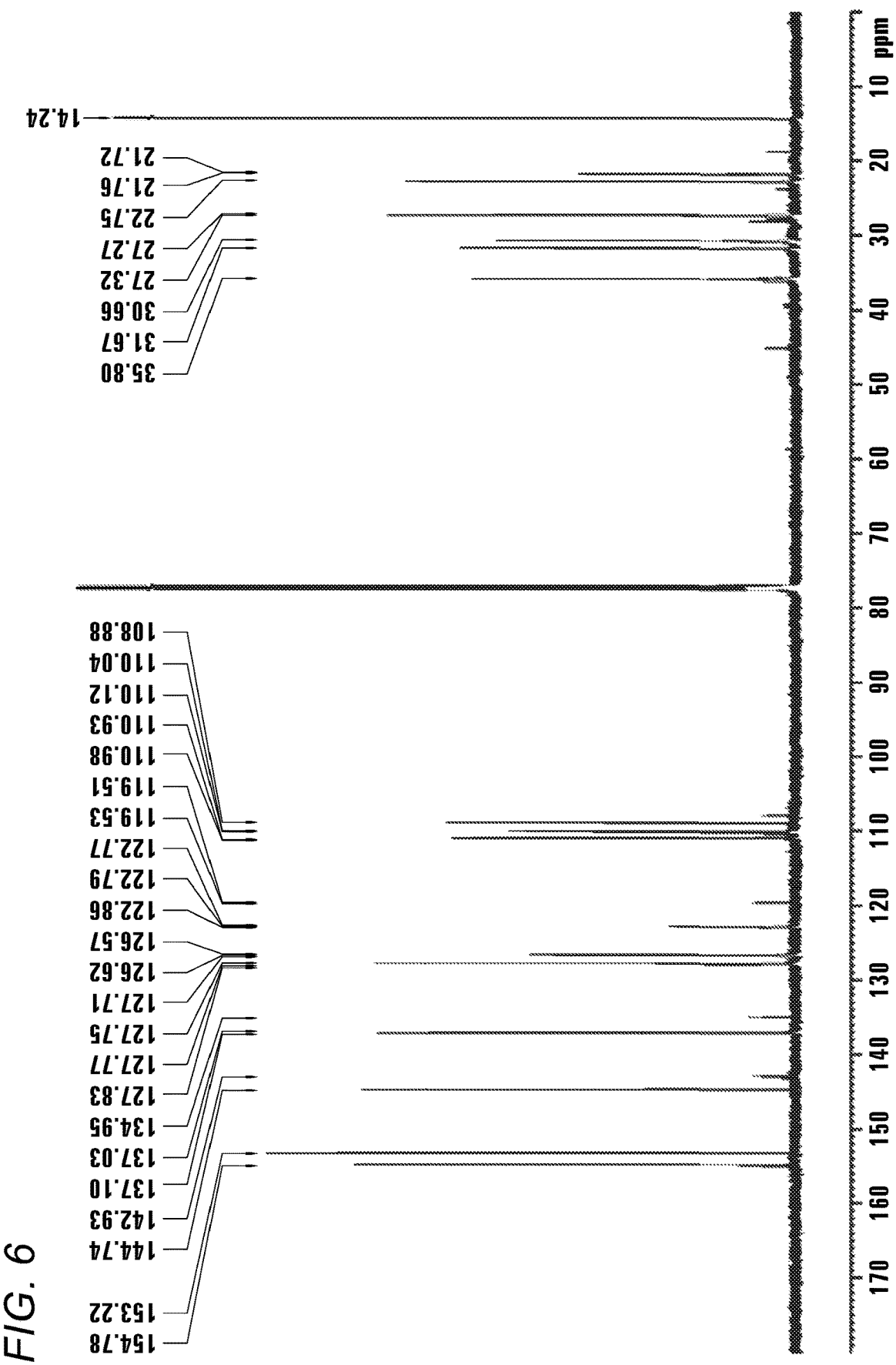
Figure 7:
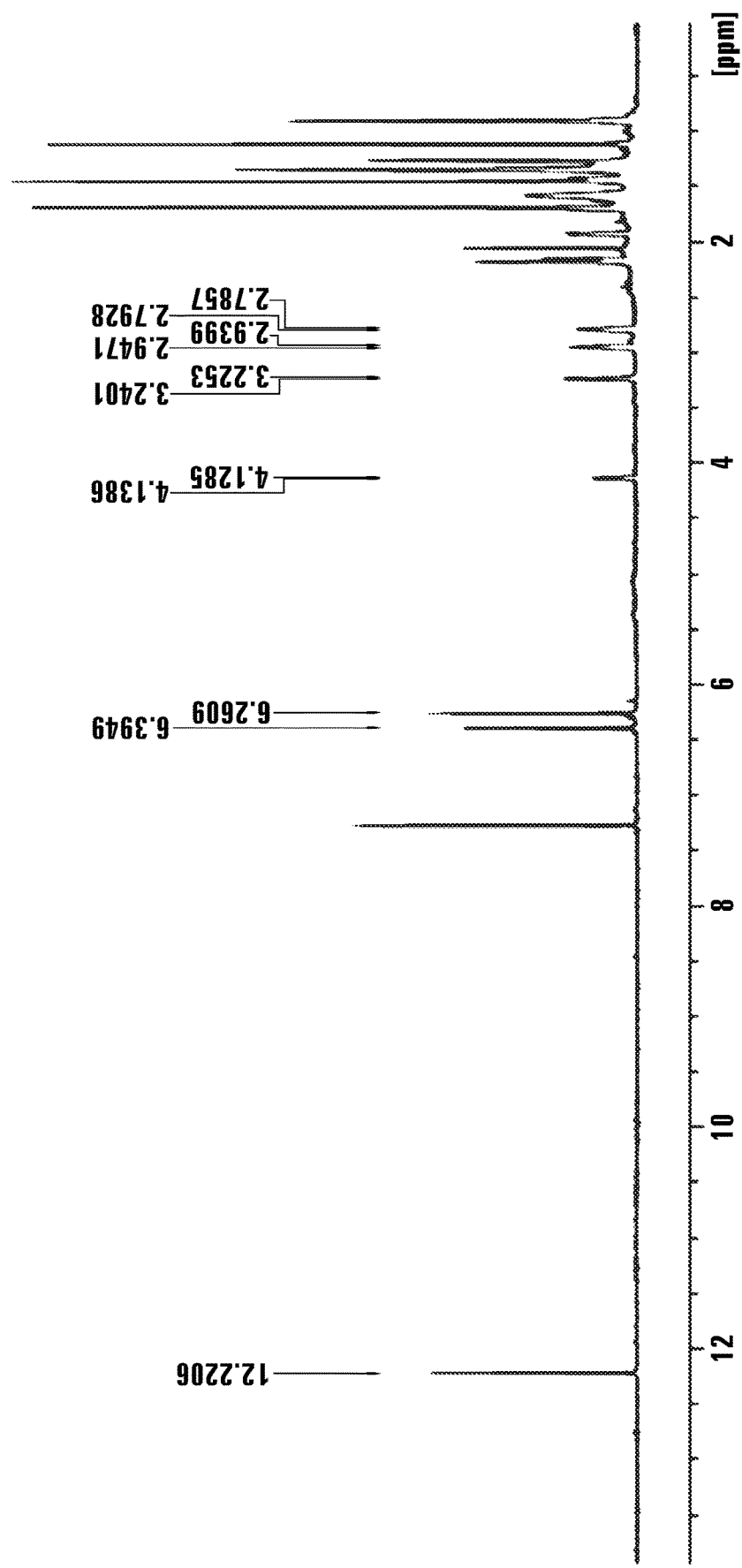
Figure 8:
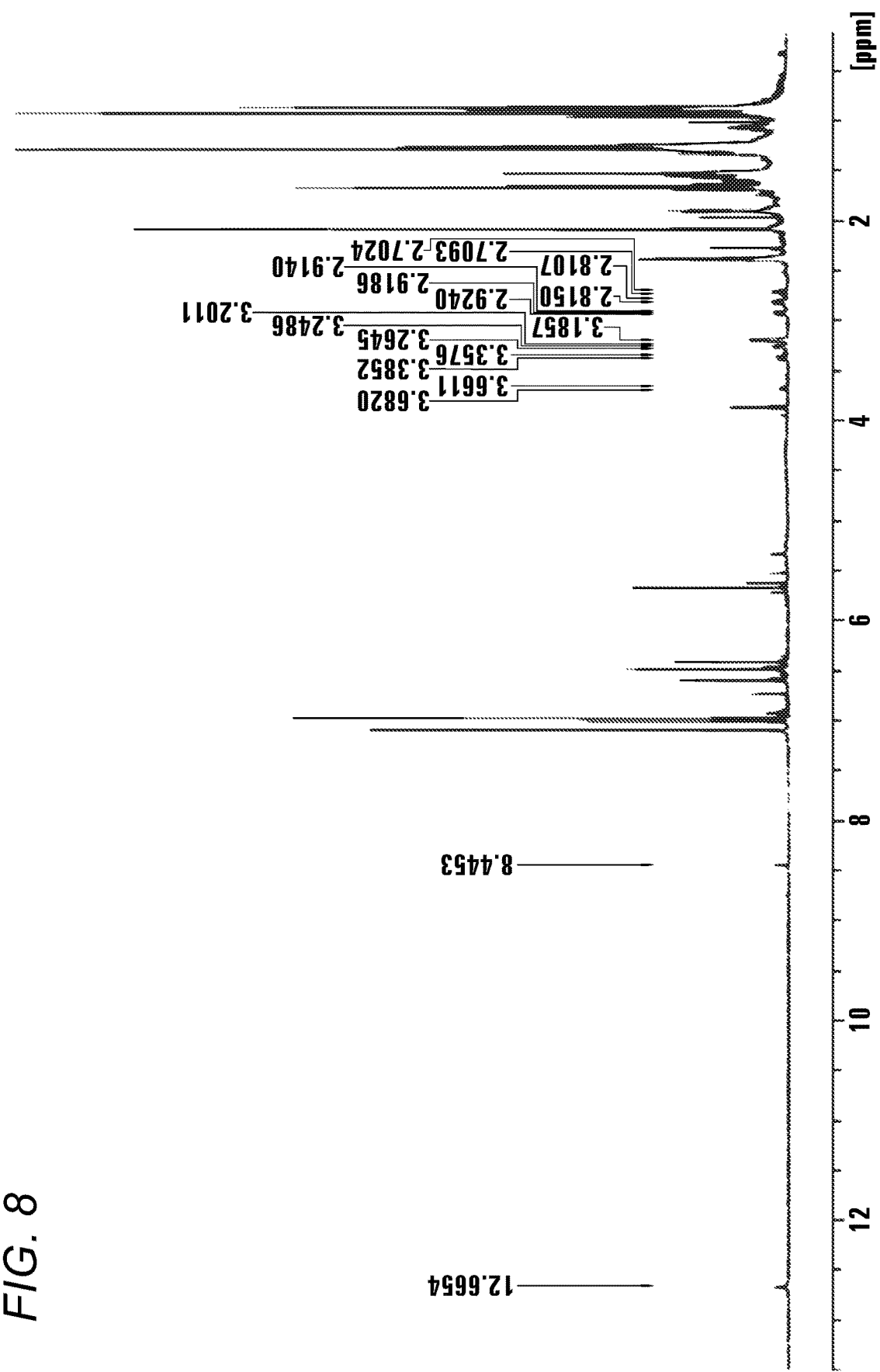
Figure 9:
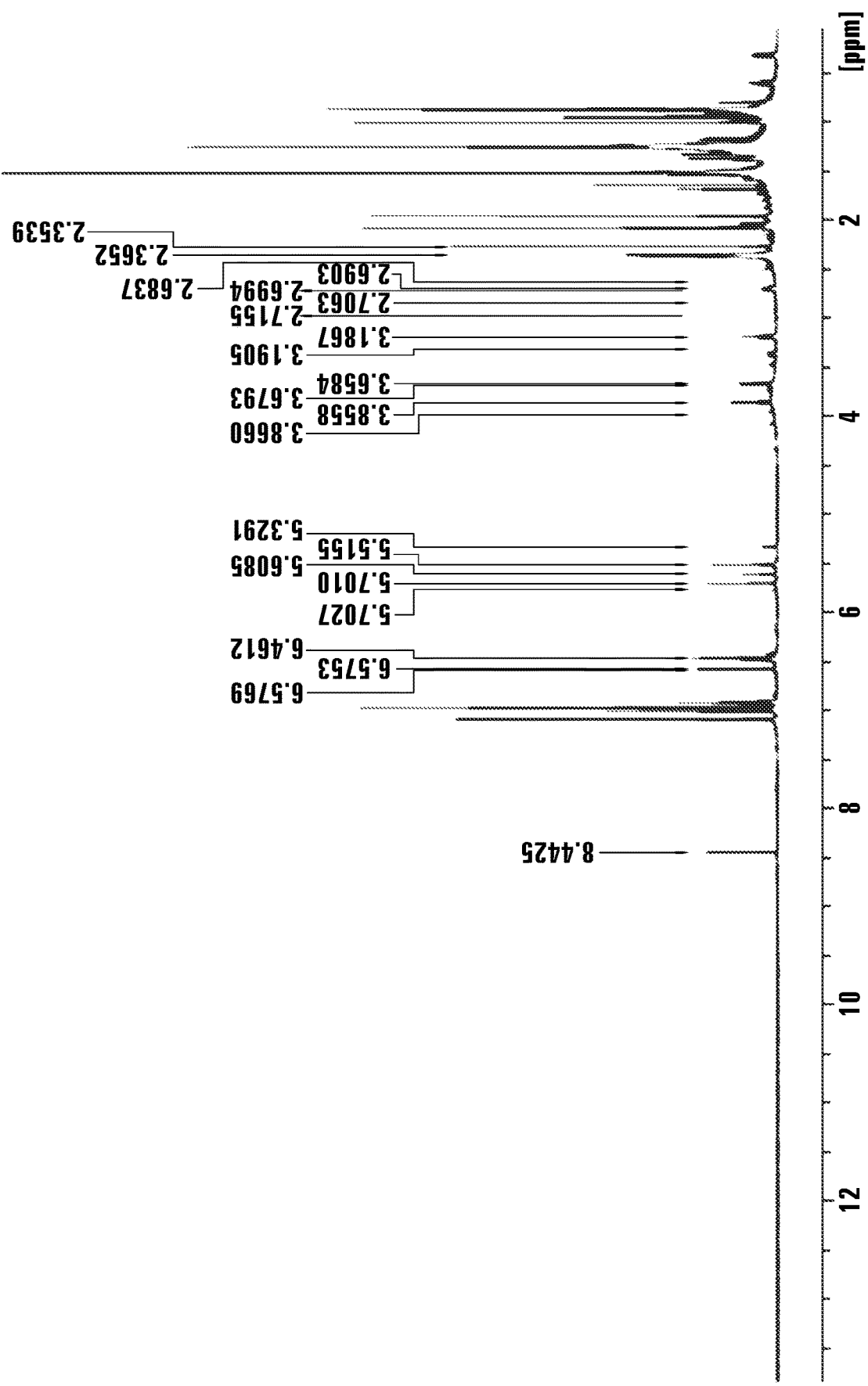
Figure 10:
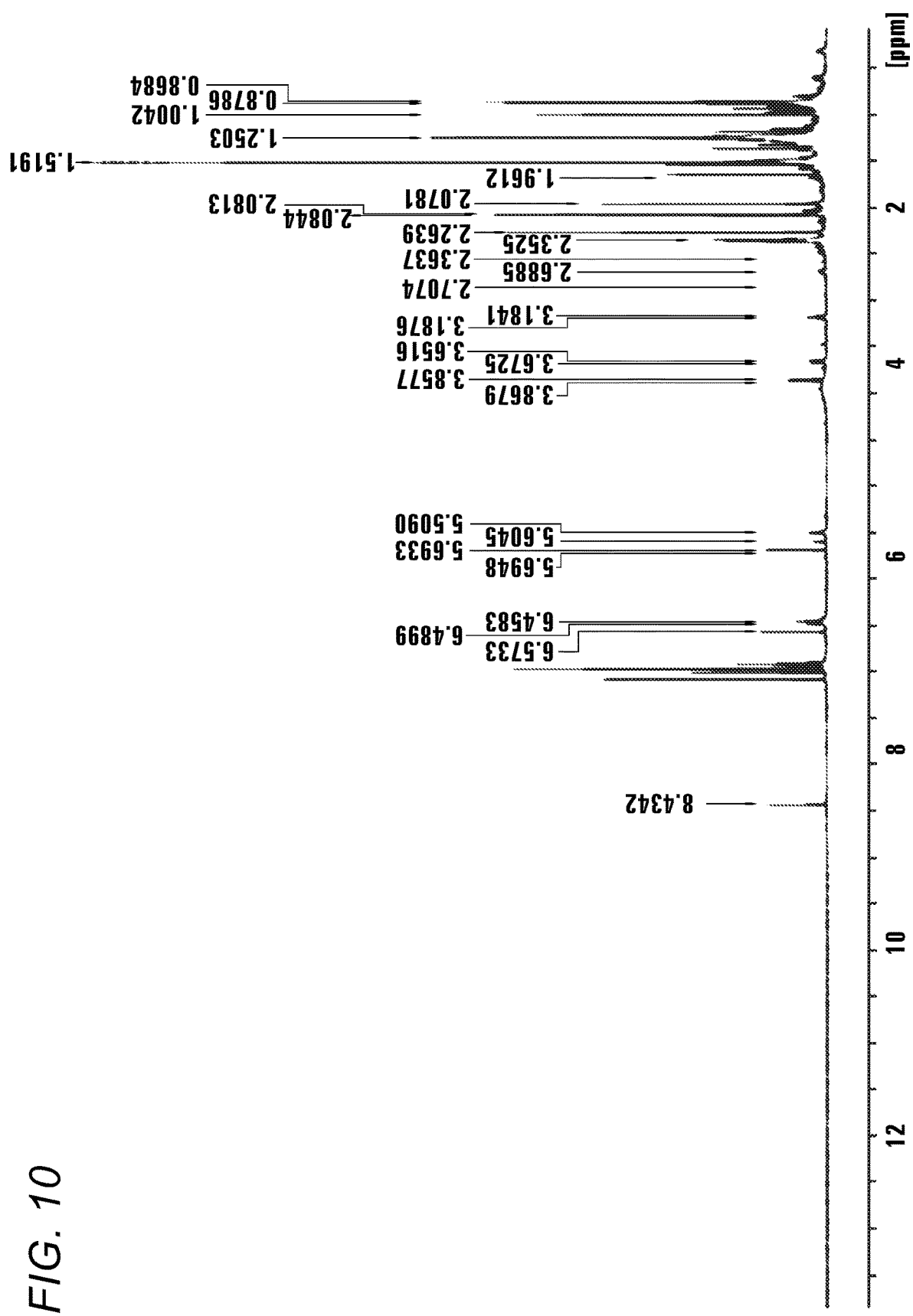
Figure 11:
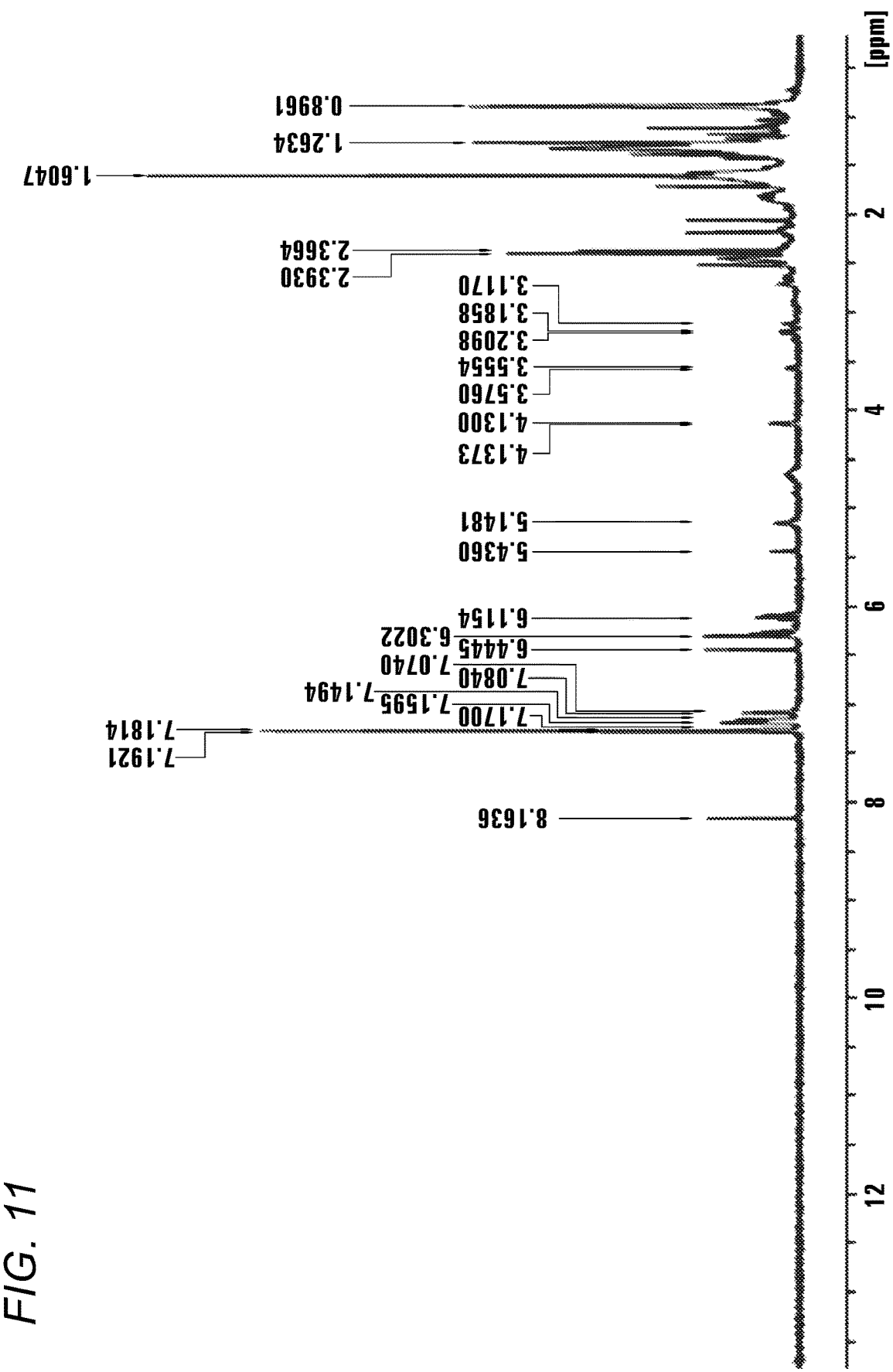
Figure 12:
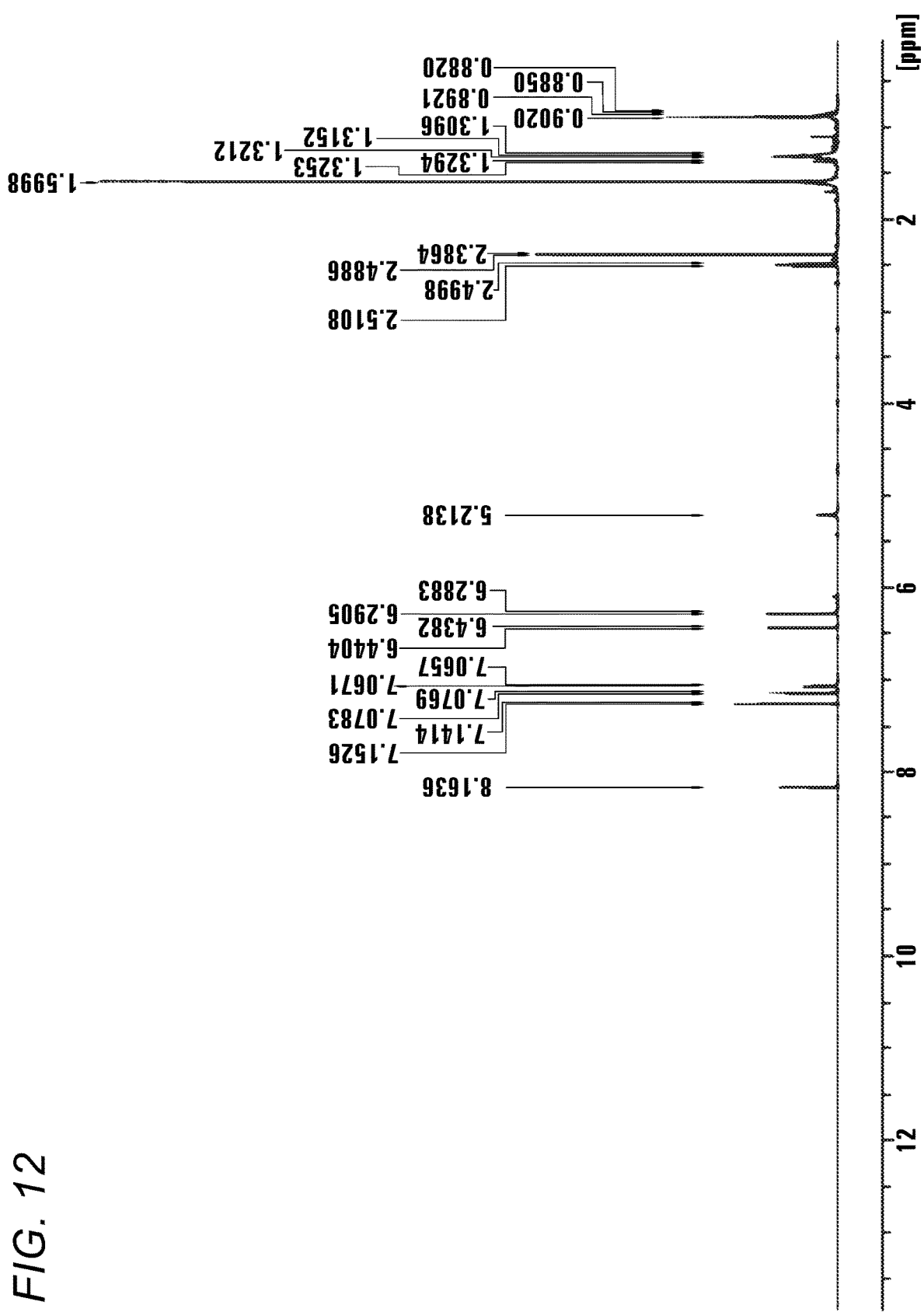
Figure 13:
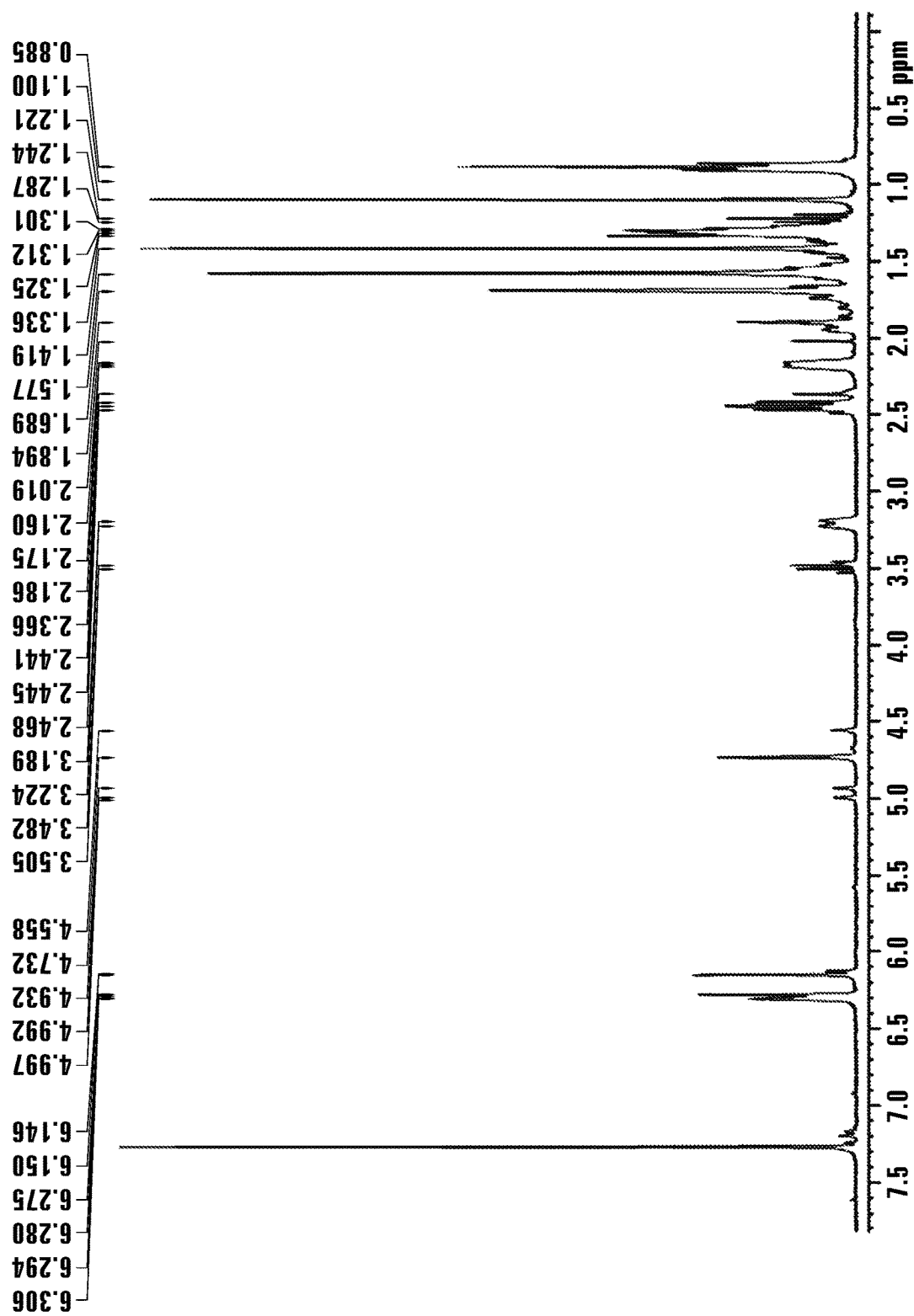
Figure 14:
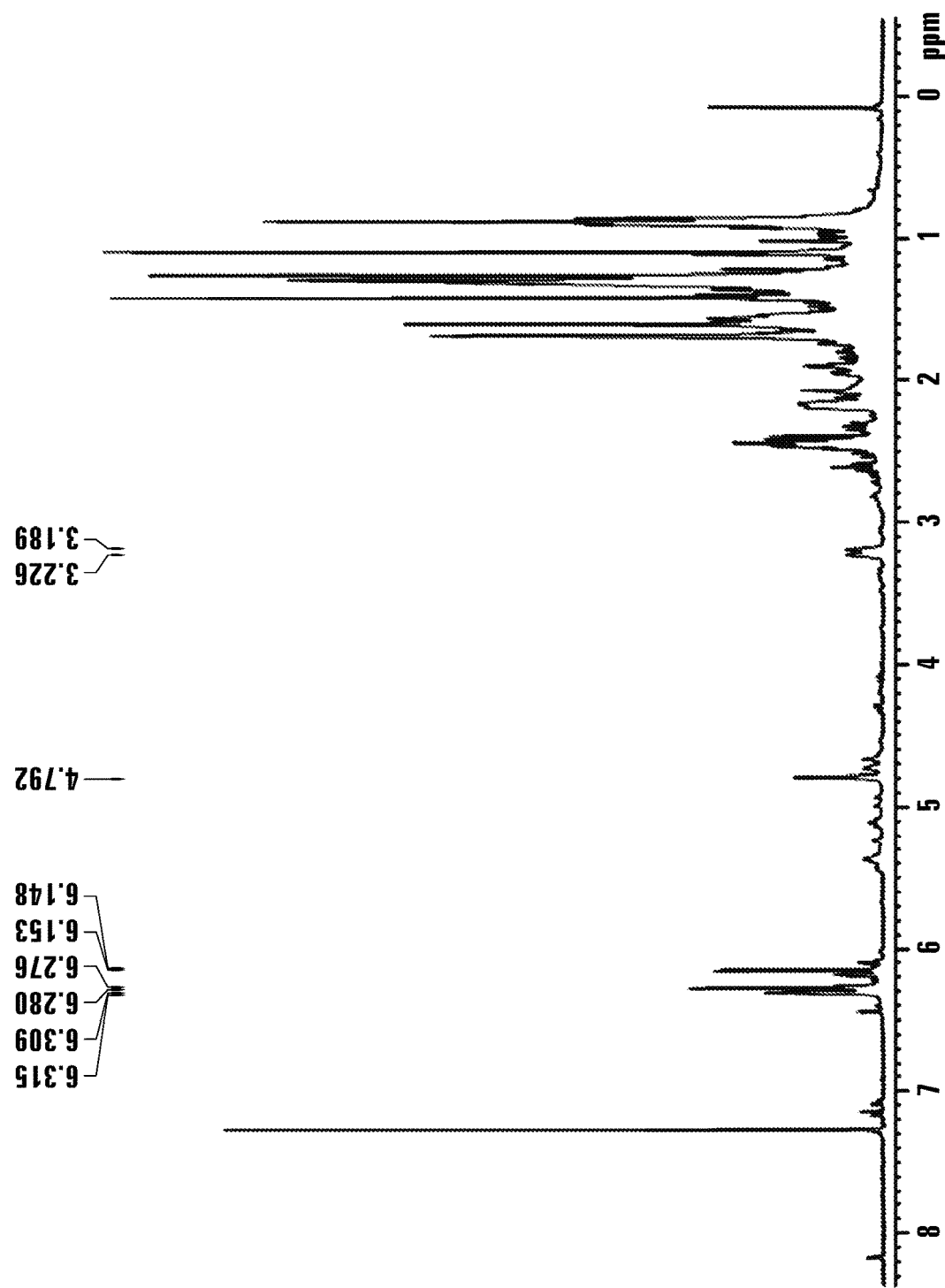

FIG. 2A is a simplified pictorial illustration of a method of extraction of compounds from cannabinoid-rich biomass, in accordance with an embodiment of the present invention;

FIG. 2B is a simplified pictorial illustration of a method for synthesizing tetrahydrocannabinol (THC) products, in accordance with an embodiment of the present invention;

FIG. 2C a simplified schematic diagram of a chemical conversion of Δ9-THC from, CBD, in accordance with an embodiment of the present invention;

FIG. 2D is a simplified pictorial illustration of a method for synthesizing cannabinol (CBN) products, in accordance with an embodiment of the present invention;

FIG. 2E a diagram of a schematic of method of producing CBN from Δ9THCa, Δ9THC, CBDa and CBD, in accordance with an embodiment of the present invention;

FIG. 2F is a simplified pictorial illustration of a method for purifying cannabinoids, in accordance with an embodiment of the present invention;

FIG. 3 is a proton NMR spectrum of a plant extract rich in THCa, in accordance with an embodiment of the present invention;

FIG. 4 is a proton NMR spectrum of the plant extract of FIG. 2A after refluxing in $I_2$/HI, in accordance with an embodiment of the present invention;

FIG. 5 is a proton NMR spectrum of CBN in certain fractions recovered with column chromatography from the plant extract of FIG. 4, in accordance with an embodiment of the present invention;

FIG. 6 is a 13C NMR spectrum of CBN in certain fractions recovered with column chromatography from the plant extract of FIG. 4, in accordance with an embodiment of the present invention;

FIG. 7 is a proton NMR spectrum of a high-THC extract prior to reaction, in accordance with an embodiment of the present invention;

FIG. 8 is a proton NMR spectrum of the high-THC extract of FIG. 7 after 1 hour of reaction, in accordance with an embodiment of the present invention;

FIG. 9 is a proton NMR spectrum of the high-THC extract of FIG. 7 after 2 hours of reaction, in accordance with an embodiment of the present invention;

FIG. 10 is a proton NMR spectrum of the high-THC extract of FIG. 7 after 4 hours of reaction, in accordance with an embodiment of the present invention;

FIG. 11 is a proton NMR spectrum of the high-THC extract of FIG. 7 after washing the reaction, in accordance with an embodiment of the present invention;

FIG. 12 is a proton NMR spectrum of the high-THC extract of FIG. 7 after purification of CBN, in accordance with an embodiment of the present invention;

FIG. 13 is an NMR spectrum of Δ9THC prepared from crystalline CBD, in accordance with an embodiment of the present invention; and FIG. 14 is an NMR spectrum of Δ9THC prepared from a plant extract with approximately 10% CBD, in accordance with an embodiment of the present invention;

In all the figures similar reference numerals identify similar parts.

DETAILED DESCRIPTION OF THE EMBODIMENTS

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

Generally, the present disclosure provides methods of extraction of phytocannabinoids from initial *cannabis* biomass, followed by the method of synthesizing Δ9THC from CBDa and CBD and the method for synthesizing CBN from Δ9THCa, Δ9THC, CBDa and CBD. The method may be applied to a reagent mixture that includes one or more of purified Δ9THCa, Δ9THC, CBDa and CBD, such as a solution of CBD distillate. The method may also be applied to a reagent mixture including Δ9THCa, Δ9THC, CBDa, CBD, other phytocannabinoids, terpenoids, phenylpropanoids and other compounds found in *C. sativa*.

FIG. 1 is a simplified illustration of prior art demonstrating steps of synthesis of CBV.

The crude extract (2 g) containing CBDVA (102) as its major phytocannabinoid was dissolved in toluene (100 mL) (104) in a round-bottom flask (106) and 200 mg of iodine was added. The solution was then refluxed at 110.6° C. (108), following the course of the reaction by TLC (petroleum ether/EtOAc, 9:1; Rf 3d=0.05, Rf 1b=0.35). Additional amounts of iodine (100 and 150 mg) were added after respectively 30 and 40 min (steps 110 and 112). After refluxing for 15 min from the last addition, the reaction was worked up by cooling to room temperature and sequentially washed with 5% $Na_2S_2O_3$ and brine. After drying, the organic phase was evaporated (114), and the residue was purified by GCC on silica gel with petroleum ether as eluant to afford 25 mg of CBN and 150 mg of cannabivarin (CBV).

FIG. 2A is a simplified pictorial illustration of a method of extraction of compounds from cannabinoid-rich biomass, in accordance with an embodiment of the present invention;

Example #I

Crude extraction includes the step of weighing biomass and crushing it with mortar and pestle. Cannabinoid-rich biomass (206) was placed into the Erlenmeyer flask (202) and toluene (204) was added to the biomass (100 mL) and the mixture was vigorously stirred for 20 minutes (208). Using Buchner funnel (210), the biomass mixture (214) was then filtered to give a golden colored toluene solution (212). This step was repeated a total of two times, the golden color of the solution drastically decreased with the subsequent washings. The combined Toluene solutions (300 mL) was used to remove all volatiles in vacuo (218) to yield a thick brown oil enriched in CBDa and THCa (216). In one specific case, using quantitative NMR, the extract was found to be 45.2% CBD-A and 1.2% THC-A.

FIG. 2B is a simplified pictorial illustration of a method for synthesizing tetrahydrocannabinol (THC) products, in accordance with an embodiment of the present invention;

Example #II

THC synthesis includes adding toluene (step 222) to CBD-A-/CBD- and THC-A/THC-rich extracts (224) such as the one described in FIG. 2A into a Teflon sealed round-bottomed flask (230) fitted with a water cooled reflux condenser and placing it an oil bath (226) on a stirring hot-plate (228). The oil bath is heated to a reflux at 130° C. for at least 2 h and the reaction then is allowed to cool to room temperature. The reflux condenser is then replaced with a Teflon sealed joint adapter and then the entire apparatus with CBD/THC-rich extract (232) is placed under vacuum, removing toluene in vacuo. Either dichloromethane (238) or chloroform (20 mL) is transferred into the flask under vacuum, after which the round bottom flask and solution are placed under an inert atmosphere. Dichloromethane used in the reaction is dried prior use with $CaH_2$, and stored under argon to keep dry. The solution is then cooled to an optimal temperature between 0° C. and −10° C. using ice or an ice/acetone bath. Under a constant flow of argon (234) to create inert atmosphere (nitrogen can be used but it is less effective), boron trifluoride etherate (236) (100 µL) is added via syringe whereupon the brown solution becomes green. The reaction is left to stir for at least 3 hours between 0° C. and −10° C. The reaction is allowed to warm to ambient temperature and at least 2 mL of aqueous saturated sodium hydrogen carbonate solution (240) is added giving a cloudy brown mixture which is left to stir for at least 30 minutes.

The reaction mixture contains two layers, the organic (244) and the aqueous (246) layers which are both filtered together using a Buchner funnel. The organic layer (248) is isolated using a separatory funnel and further washed with aqueous saturated sodium hydrogen carbonate solution (3×10 mL) before being dried with magnesium sulfate. Volatile compounds are removed in vacuo (250) to produce a dark green residue. The residue (THC-rich extract, 256) is purified using column chromatography. Silica gel was used as the stationary phase (30 mL) and a 85:15 solution of petroleum ether:diethyl ether as the eluent. Several compounds separate out of the residue, (−)-trans-$\Delta^9$-tetrahydrocannabinol would come out as the third product. The fractions containing (−)-trans-$\Delta^9$-tetrahydrocannabinol are combined and solvents are removed in vacuo to produce a dark yellow oil, $^1$H and $^{13}$C NMR data are consistent with previously reported values ($R_f$=0.66).

FIG. 2C a simplified schematic diagram of a chemical conversion of Δ9-THC from CBD, in accordance with an embodiment of the present invention.

FIG. 2D is a simplified pictorial illustration of a method for synthesizing CBN products, in accordance with an embodiment of the present invention.

Example #III

Into a 100 mL round bottom flask (230) with a Teflon stir bar, iodine (282.3 mg, 1.1 mmol) was weighed out. Extract from *Cannabis Sativa* (564.5 mg) (224) was dissolved in toluene (20 mL) (222) and added to the flask creating a dark red/brown solution, the reaction flask was then fitted with a reflux condenser. The flask was submerged into an oil bath (226) and heated to 130° C. (228) which was sufficient to cause the toluene to reflux. The reaction was allowed to stir under reflux for 3 hours. The reaction flask was left to cool to room temperature and washed with a saturated solution of sodium thiosulfate (3×30 mL). The combined aqueous layer was then washed with toluene (20 mL) and the organic layers combined and dried with magnesium sulfate. Volatile compounds were removed in vacuo to produce a crude brown oil. The oil was purified using column chromatography. Silica gel was used as the stationary phase (30 mL) and a 9:1 solution of petroleum ether:diethyl ether as the eluent. The cannabinol was observed to move through the column as the fourth fraction, observed via thin layer chromatography ($R_f$=0.27). The appropriate samples were combined and solvents were removed in vacuo to produce cannabinol as an orange oil (262), $^1$H and $^{13}$C NMR data were consistent with previously reported values[1] (138.2 mg).

In comparison to prior art (FIG. 1), this method contains fewer steps (so called "one-step") reaction, uses less iodine and results in the higher amount of CBN produced.

FIG. 2E a diagram of a schematic of method of producing CBN from Δ9THCa, Δ9THC, CBDa and CBD, in accordance with an embodiment of the present invention.

Quantification of CBN and other phytocannabinoids was completed by H$^1$ NMR. The characteristic peaks of several phytocannabinoids are shown in Table 1.

TABLE 1

Characteristic Peaks of Phytocannabinoids by H$^1$ NMR.

| Phytocannabinoid | Characteristic peak(s) in CDCl$_3$ |
|---|---|
| CBD | 5.99, 5.02 ppm as broad singlets of —OH |
| CBDa | 11.93 ppm as a singlet |
| Δ9THC | 6.14 ppm as a doublet, also need —OH peak around 4.87 ppm |
| THCa | 12.19 ppm as a singlet |
| Δ8THC | 2.70 ppm as a triplet of doublets, also need —OH peak around 4.82 ppm |
| CBN | 8.16 ppm as a singlet |

The yield of CBN was observed to be between about 17 and 22% w/w compared with the initial weight of the extract, which was estimated to be up to 70% phytocannabinoids. In some embodiments, the purity of the CBN in the extract was determined to be at least 70%. In some embodiments, the purity was between 70 and 85%.

The purity of CBN in the material recovered, as determined by NMR, GC-MS and HPLC, is greater than 80%, and in some cases greater than 90%.

FIG. 2F is a simplified pictorial illustration of a method for purifying cannabinoids, in accordance with an embodiment of the present invention;

The oil was purified using column chromatography (275). Silica gel (276) was used as the stationary phase (30 mL) and a 9:1 or 8:2 solution of petroleum ether:diethyl ether as the eluent was added to crude extract (274) using the funnel (273). A number of fractions can be collected (277, 278, 279) can be collected into a beaker. For example, in the case of conversion of CBD to THC, (−)-trans-$\Delta^9$-tetrahydrocannabinol would come out as the third product. In the case of cannabinol synthesis, it moves through the column as the fourth fraction. Organic solvent is then removed under a vacuum to give the desired product (280).

Samples of the purified compounds, and a sample of the extract prior to the reaction, were prepared for analysis on by nuclear magnetic resonance ("NMR"). The samples were dissolved in deuterated chloroform for NMR spectroscopy. NMR spectra were recorded on a 700 MHz Bruker Avance II (ultrashield) spectrometer. Proton NMR was carried out at a frequency of 700.13 MHz. 13C{1H} NMR was carried out at a frequency of 176.05 MHz. All samples were referenced relative to SiMe$_4$ through the residual solvent resonance(s) for 1H and 13C{1H}. All NMR spectra were recorded at an ambient temperature of 25° C. unless otherwise specified.

FIG. 3 is a proton NMR spectrum of a plant extract rich in Δ9THCa. A major component of the extract is Δ9THCa, as observed with the carboxylic acid peak at 12.22 ppm. Other phytocannabinoids are likely within sample but are not observed in large quantities, and there is no clear presence of Δ9THC, CBD, CBDa or CBN. Ethyl acetate solvent peaks are also visible.

FIG. 4 is a proton NMR spectrum of the reaction mixture after reflux, washing and separation. The Δ9THCa peak at 12.22 ppm has disappeared. The CBN peak at 8.16 ppm has appeared. The number of other peaks indicates that the product is not pure CBN.

FIGS. 3 and 4 show the $^1$H NMR spectrum of reaction mixture, and of the CBN fraction collected with column chromatography, respectively. The $^1$H NMR spectrum was consistent with previously reported values for CBN. The estimated yield of the extract is between 17.5 and 22.5% from the total weight of the biomass, which is 70 and 85% yield from the total amount of cannabinoids in that biomass. The estimated purity is over 90% pure CBN. Other small molecules appear to be present, likely including terpenoids and other phytocannabinoids. Characteristic peaks for Δ9THCa (12.22 PPM) Δ9THC (6.14 and 4.87 PPM), CBDa (11.93 PPM) and CBD (5.99 and 5.02 PPM) are absent from the $^1$H NMR spectrum. The $^{13}$C NMR data of the CBN faction was also consistent with the spectra of CBN (FIG. 5).

FIG. 5 is a proton NMR spectrum of the third compound eluting in fractions 25 to 43 of the column chromatograph. The peak at 8.16 ppm indicates that the fractions include primarily CBN. No presence of Δ9THCa, Δ9THC, CBDa, CBD or any other major phytocannabinoid. Minor impurities observed as small peaks between 7 and 0.5 ppm.

FIG. 6 is a $^{13}$C NMR spectrum of the third compound eluting in fractions 25 to 43 of the column chromatograph. The peak at 154.78 ppm indicates that the fractions include primarily CBN. No presence of Δ9THCa, Δ9THC, CBDa, CBD or any other major phytocannabinoid. Minor impurities observed as small peaks between 150 and 15 ppm.

Example IV

The method of Example III was applied to 508.4 mg of an extract high in Δ9THCa.

FIG. 7 shows the extract in CDCl$_3$. As shown by the peak at 12.22, this sample includes a significant amount of Δ9THCa, with a minor Δ9THC peak at 6.0 PPM and no CBN visible.

FIG. 8 shows the extract in toluene after 1 hour of reflux at a bath setting of 115° C. The reflux cannot be conducted using CDCl$_3$ as it cannot reach the required temperature for decarboxylation. As a result, the peaks have shifted relative to their CDCl$_3$ reference values. The peak at 12.7 PPM is likely Δ9THCa and the peak at 8.44 PPM is likely CBN.

FIG. 9 shows the extract in toluene after 2 hours of reflux at a bath setting of 115° C. The peak at 12.7 PPM from FIG. 8 has disappeared. The peak at 8.44 PPM has grown.

FIG. 10 shows the extract in toluene after 4 hours of reflux at a bath setting of 115° C. Very little has changed relative to the results of FIG. 9.

FIG. 11 shows the sample from FIG. 10 in CDCl$_3$ after washing. The peak at 8.16 PPM is primarily CBN. The characteristic peaks for CBDa, CBD, Δ9THCa, Δ9THC and Δ8THC are absent.

FIG. 12 shows the sample from FIG. 11 after column separation, showing an 80% pure CBN sample. There are some impurities close to the baseline but not are identifiable phytocannabinoids.

In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

The described synthetic approaches are the preferred methods that produced the highest yield from their respective starting materials. Anhydrous sodium sulfate or another suitable drying or dehydration agent known can be used in place of the magnesium sulfate. Other alkali metal hydrogen carbonate or carbonates of an alkali metal may be used instead of sodium hydrogen carbonate for the saturated aqueous solution used to neutralize and wash the reactions. With lower reaction temperatures, longer reaction times are required to achieve a comparable yield. Other solvents may be applied. Chloroform and dichloromethane provided the greatest ratio of Δ9THC to Δ8THC of the solvents that were assessed. Δ8THC and CBD persist as major by-products at temperatures above 0° C. and when using solvents other than chloroform and dichloromethane. The above procedures describe purification methods assuming the ideal procedures have been followed.

The catalyst may be any suitable Lewis acid, such as, p-toluenesulfonic acid, boron trifluoride, or BF$_3$Et$_2$O, or any suitable classical acids to the extent those are not Lewis acids, such as HCl or H$_2$SO$_4$. Reaction of CBD with non-polar Lewis acids may be in any suitable organic solvent, such as methylene chloride, ethyl acetate, ethanol or hexane. The catalyst may be HCl in ethanol or sulfuric acid in cyclohexane.

A weak base may be added to the reaction mixture prior to allowing the reaction mixture to separate into organic and aqueous phases. The base may be an alkali metal hydrogen carbonate or a carbonate of an alkali metal.

The organic layer may be dried prior to eluting. A suitable drying or dehydration compound, such as MgSO$_4$ or Na$_2$SO$_4$ may be used for drying.

The reaction may be carried out in a nitrogen atmosphere.

The yield of conversion of CBD to Δ9THC is at least 60%. In some embodiments, the yield is at least 70%. In some embodiments, the yield is between 70 and 85%. Purity of the product (determined by GC-MS and HPLC) was greater than 90%. In some embodiments, the purity is greater than 95%. In some embodiments, the purity is greater than 97%.

SOME ADDITIONAL NON-LIMITING EXAMPLES ARE PROVIDED HEREINBELOW

Example V

Reaction described in Example II was carried out under an inert atmosphere (either nitrogen or argon) with the rigorous exclusion of oxygen and water using a double manifold high vacuum line equipped with Teflon needle valves (Kontes).

The dichloromethane was dried with calcium dihydride, degassed via three freeze-pump-thaw cycles, distilled under vacuum, and stored over 4 Å molecular sieves under an argon atmosphere. Samples for nuclear magnetic resonance ("NMR") spectroscopy were recorded on a 300 MHz Bruker Avance II (ultrashield) spectrometer ($^1$H 300.13 MHz and $^{13}$C{$^1$H} 75.47 MHz) and referenced relative to SiMe$_4$ through the residual solvent resonance(s) for $^1$H and $^{13}$C{$^1$H}. All NMR spectra were recorded at ambient temperature (25° C.) unless specified otherwise. Powdered crystalline CBD was used as a standard. All solvents and the catalyst were obtained from Aldrich Chemicals and used as received.

Crystalline CBD (281 mg, 0.894 mmol) was added to a 100 mL, 2 necked round bottom flask fitted with a Teflon sealed joint adapter and then the entire apparatus was placed under vacuum. Dichloromethane (20 mL) was transferred into the flask under vacuum, after which the round bottom flask and solution were placed under an inert atmosphere.

The solution was cooled to an optimal temperature between −10° C. and 0° C. using ice or an ice/acetone bath, such as a 1:1 ice-acetone bath. Under a constant flow of either nitrogen or argon, boron trifluoride etherate (46 μL, 0.375 mmol) was added into the stirring solution with a syringe. The reaction was left to stir for at least 3 hours at −10° C., resulting in a red solution. The reaction mixture was allowed to warm to ambient temperature and at least 2 mL of aqueous saturated sodium hydrogen carbonate solution was added giving a cloudy white mixture which was left to stir for 30 minutes.

After stirring for 30 minutes, the reaction mixture contained two layers, an organic layer and an aqueous layer. The organic layer was isolated using a separation funnel and further washed with deionized water (3×10 mL) before being dried with magnesium sulfate.

Volatile compounds were removed in vacuo to produce a crude thick light-yellow oil. The oil was purified using column chromatography. Silica gel was used as the stationary phase (30 mL) and a 1:1 solution of petroleum ether: diethyl ether as the eluent. The Δ9THC was observed to move through the column as a light-yellow fraction which was collected separately. Solvents were removed in vacuo to produce Δ9THC as a dark yellow oil.

FIG. 13 is an $^1$H NMR spectrum of the Δ9THC fraction collected with column chromatography. These results are consistent with previously reported values ($R_f$=0.89, 202 mg, 71.9%). The characteristic Δ9THC peak at 3.49 ppm is visible in FIG. 13. The $^{13}$C NMR data was also consistent with the spectra of Δ9THC (data not shown). Characteristic peaks for Δ8THC and CBD are absent from the $^1$H NMR spectrum. Ethyl acetate solvent peaks are also visible in FIG. 13.

Example VI

Reaction described in Example V was modified by use of chloroform rather than dichloromethane. The results were similar to the results described in Example V.

Example VII

Reaction described in Example V I was performed at −20° C. with a six-hour reaction time instead of three hours. The results were similar to the results described in Example V.

Example VIII

*Cannabis* extract was prepared from flowers of several *Cannabis sativa* lines, with an average CBD concentration of about 10% w/w in the flowers (as tested with HPLC). Flowers were dried to 15-18% moisture content and ground to powder consistency. Extraction was done with ACS grade ethyl acetate from Fisher Scientific (cat #E145-4, 99.9% pure). Powdered plant tissue was weighed to 3 g using an analytical balance. The plant material was placed inside a 250 mL Erlenmeyer flask. Ethyl acetate (100 mL) was poured into the flask with the plant material. The flask was then wrapped with tin foil and shaken continuously (120 rpm) in an incubator at 210° C. overnight and in the dark.

After overnight solvent extraction, the resulting extract was filtered through cotton into a 100 mL round bottom flask. The extract was concentrated to a volume of about 2 to 3 mL using a rotary vacuum evaporator. The extract was then transferred to a tared 3 dram vial (cat #60975L Kimble from Fisher Scientific). The leftover solvent was evaporated to dryness in an oven overnight at 500° C. to eliminate the solvent completely. The mass of each extract was recorded.

Each sample of the extract was estimated to be in the range of 8 to 12% w/w CBD. The reagents were based on a 10% w/t and used in slight excess to accommodate other materials and competing reactions with other molecules in the extract. An ideal example has been presented based on an estimation that the extract as about 10% CBD.

*Cannabis* extract (570 mg, 10% w/w CBD or 57.0 mg) was added to a 100 mL, 2 necked round bottom flask fitted with a Teflon sealed joint adapter and then the entire apparatus was placed under vacuum. Dichloromethane (20 mL) was transferred into the flask under vacuum, after which the round bottom flask and solution were placed under an inert atmosphere.

The solution was cooled to an optimal temperature between −10° C. and 0° C. using ice or an ice/acetone bath, such as a 1:1 ice-acetone bath. Under a constant flow of either nitrogen or argon, boron trifluoride etherate (54 μL, 0.439 mmol) was added via syringe whereupon the brown solution became green. The reaction was left to stir for at least 3 hours at a temperature between −10° C. and 0° C. The reaction mixture was allowed to warm to ambient temperature and at least 2 mL of aqueous saturated sodium hydrogen carbonate solution was added giving a cloudy brown mixture which was left to stir for 30 minutes.

After stirring for 30 minutes, the reaction mixture contained two layers, an organic layer and an aqueous layer, which were both filtered together using a Buchner funnel. The organic layer was isolated using a separation funnel and further washed with aqueous saturated sodium hydrogen carbonate solution (3×10 mL) before being dried with magnesium sulfate.

Volatile compounds were removed in vacuo to produce a dark green residue. The residue was purified using column chromatography. Silica gel was used as the stationary phase (30 mL) and an 85:15 solution of petroleum ether:diethyl ether as the eluent.

Several compounds separate out of the residue. Δ9THC was the third product. The fractions containing Δ9THC were combined and solvents were removed in vacuo to produce a dark yellow oil. Small amounts of impurities persist with this method.

The characteristic Δ9THC peak at 3.49 ppm is visible in FIG. 14. Characteristic peaks for Δ8THC and CBD are absent from the Δ9THC fraction. Ethyl acetate solvent peaks are also visible in FIG. 14.

FIG. 14 is an $^1$H NMR spectrum of the Δ9THC fraction collected with column chromatography. The $^1$H NMR spectrum was consistent with previously reported values for Δ9THC (Rf=0.66, 25.0 mg). The characteristic Δ9THC peak at 3.49 ppm is visible in FIG. 14. The estimated yield of the extract is about 70% pure Δ9THC. Other small molecules appear to be present, likely include terpenoids. The $^{13}$C NMR data was also consistent with the spectra of Δ9THC (data not shown). Characteristic peaks for Δ8THC and CBD are absent from the $^1$H NMR spectrum. Ethyl acetate solvent peaks are also visible in FIG. 14.

In some cases, these drugs are different extracts from the same Hemp strains. In some cases, these drugs are derived drugs from different Hemp strains. In some cases, these drugs are combination therapies from different Hemp strains. In some cases, these drugs are combinations of extracts from different Hemp strains. In some cases, these drugs are combinations of extracts from different Hemp strains and at least one known pharmaceutical drug. In some cases, these drugs are combinations of extracts from different Hemp strains and at least one known FDA-approved pharmaceutical drug. In some cases, the extracts are water-soluble. In other cases, the extracts are in one or more organic solvents. In yet other cases, the extracts are in one or more oils.

Advantages of the Present Invention Over the Prior Art

Extraction Steps

In general, the biomass extraction method of the present invention has fewer steps, and thus, is faster and more efficient than the prior art methods.

Moreover, a one-pot procedure is employed, in which the residual toluene used for extraction, does not create a problem since the toluene is then used for the preparation of CBN. In contrast, when ethanol or acetone are used for extraction, per the prior art methods, the ethanol/acetone must be removed, prior to the use of a different solvent in the next step.

In addition, toluene presents the advantage over ethanol or acetone as it gives better efficiency in the extraction of non-polar molecules such as cannabinoids and terpenoids.

According to some embodiments, toluene could potentially be replaced with xylene (dimethylbenzene) but it would be more difficult to remove under vacuum, as it has a higher boiling point than toluene.

Toluene is better to use over ethanol as a higher temperature with lower pressure can be used for the same effect, as it has a higher boiling point.

CBD to THC Conversion

The main differentiator is the use of extract enriched with CBD rather than crystalline CBD—it is much more difficult to achieve CBD to THC conversion in a complex mixture.

The use of hydrocarbon-greased ground glass joints, as compared to simple nasal/hose joints described in prior art establishes a more rigorous approach which is more air-tight.

Another distinguishing point is that the reactions of the present invention were conducted under argon (rather than nitrogen, per the prior art). Being denser, argon flushes the initial atmosphere better and sits over the liquid tighter than nitrogen. This is specifically important for larger scale reaction, where nitrogen would require longer time to be as efficient.

Additionally, the solvent employed in CBD to THC conversion method of the present invention is methylene chloride (CH2Cl2) is dried with CaH2 and stored under nitrogen/argon atmosphere to be kept extra-dry.

CBD to CBN Conversion

Our main advantage is that the method of the present invention is, according to some embodiments, a one-step method. First, the present invention method uses the biomass extracted with toluene and do not need to remove all of the toluene since the conversion is also performed in toluene. Second, the reaction is literally a one-pot reaction, whereas in previous art requires multiple steps of adding different ingredients (see FIG. 1).

The present invention methods use high concentration of CBD in biomass extracts and specifically demonstrate to obtain a high quantity of CBN, whereas prior art used high CBD-V extract and mainly obtained CBN-V with only small amounts of CBN.

In the present invention reaction, a pressurized container is used, which allows achievement of a higher reaction temperature 130° C., as compared to performing the reaction in refluxing toluene (111° C.) in prior art processes.

The references cited herein teach many principles that are applicable to the present invention. Therefore, the full contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

REFERENCES

Choi, Y. H.; Hazekamp, A.; Peltenburg-Looman, A. M. G.; Frederich, M.; Erkelens, C.; Lefeber, A. W. M.; Verpoorte, R. (2004), "NMR assignments of the major cannabinoids and cannabiflavonoids isolated from flowers of *Cannabis sativa*" *Phytochemical Analysis*, 15: 345 to 354.

Gaoni and Mechoulam (1966) "Hashish-VII: The isomerization of cannabidiol to tetrahydrocannabinols", *Tetrahedron* 22(4): 1481-1488.

Pollastro F, Caprioglio D, Marotta P, Moriello A S, De Petrocellis L, Taglialatela-Scafati O, Appendino G. (2018) "Iodine-Promoted Aromatization of p-Menthane-Type Phytocannabinoids" *J Nat Prod*, 81(3): 630-633.

Repka M A, ElSohly M A, Munjal M, Ross S A. (2006) "Temperature stability and bioadhesive properties of delta9-tetrahydrocannabinol incorporated hydroxypropylcellulose polymer matrix systems" *Drug Dev Ind Pharm*, 32(1): 21-

The invention claimed is:

1. A method of purifying cannabinol comprising:
   a) reacting cannabis with a reagent mixture comprising toluene, sodium hydrogen carbonate and dichloromethane at a temperature of at least 100° C. in a w/w ratio of at least 30% of iodine relative to the cannabis for one to four hours to form a product mixture; and
   b) eluting under vacuum the product mixture to produce cannabinol of a purity of at least 80% at a yield of at least 80% by weight of the cannabinol in said cannabis.

2. The method of claim 1, wherein the product mixture comprises an extract from *Cannabis sativa*.

3. The method of claim 1, wherein the reacting step is a "one-step" reaction.

4. The method of claim 1, wherein the product mixture comprises at least one phytocannabinoid.

5. The method of claim 1, wherein the reagent mixture comprises iodine.

6. The method of claim 1, wherein said temperature is 130° C.

7. The method of claim 1, wherein said cannabinol is of a purity of at least 85%, at least 90%, at least 91%, at least 92%, at least 93%, at least 94%, at least 95%, at least 96%, at least 97%, at least 98% or at least 99%.

8. The method of claim 1, wherein said yield of cannabinol is at least 12%, at least 14%, at least 16%, at least 18%, or at least 20% of the total weight of said cannabis sativa used.

9. The method of claim 1, further comprising drying said cannabinol of a purity of at least 80% with at least one drying agent.

10. The method of claim 9, wherein said at least one drying agent comprises magnesium sulfate.

11. The method of claim 1, further comprising purifying the cannabinol with column chromatography, using silica gel as the stationary phase and a 9:1 solution of petroleum ether:diethyl ether as the eluent.

* * * * *